United States Patent
Berliner

(12) United States Patent    (10) Patent No.: US 6,922,479 B2
Berliner    (45) Date of Patent: Jul. 26, 2005

(54) SYSTEM AND METHOD FOR GENERATING A PROFILE OF PARTICULATE COMPONENTS OF A BODY FLUID SAMPLE

(75) Inventor: Shlomo Berliner, Givatayim (IL)

(73) Assignee: Inflamet Ltd., Tel Aviv (IL)

( * ) Notice: Subject to any disclaimer, the term of this patent is extended or adjusted under 35 U.S.C. 154(b) by 570 days.

(21) Appl. No.: 09/818,855

(22) Filed: Mar. 28, 2001

(65) Prior Publication Data

US 2002/0001402 A1 Jan. 3, 2002

Related U.S. Application Data

(63) Continuation-in-part of application No. PCT/IL00/00673, filed on Oct. 23, 2000.

(30) Foreign Application Priority Data

Nov. 1, 1999 (IL) .................................................. 132687

(51) Int. Cl.⁷ .............................................. G06K 9/00
(52) U.S. Cl. ........................ 382/134; 600/309; 356/39
(58) Field of Search ................................ 382/133, 134, 382/128, 129; 377/10; 702/26; 600/309, 320, 322, 468; 436/520, 532; 73/53.01, 105, 1.01; 435/4–5; 356/39–40; 359/393

(56) References Cited

U.S. PATENT DOCUMENTS

| | | | | | |
|---|---|---|---|---|---|
| 4,741,043 | A | * | 4/1988 | Bacus | 382/129 |
| 5,000,554 | A | * | 3/1991 | Gibbs | 359/393 |
| 5,428,690 | A | * | 6/1995 | Bacus et al. | 382/128 |
| 5,460,945 | A | * | 10/1995 | Springer et al. | 435/7.24 |
| 5,686,309 | A | * | 11/1997 | Frank et al. | 436/66 |
| 5,822,447 | A | * | 10/1998 | Kasdan | 382/133 |
| 5,878,160 | A | * | 3/1999 | Horiuchi et al. | 382/133 |
| 5,976,786 | A | * | 11/1999 | Finkel et al. | 435/5 |
| 6,203,487 | B1 | * | 3/2001 | Consigny | 600/12 |
| 6,571,117 | B1 | * | 5/2003 | Marbach | 600/473 |
| 6,687,395 | B1 | * | 2/2004 | Dietz et al. | 382/133 |
| 2003/0022393 | A1 | * | 1/2003 | Seul et al. | 436/518 |
| 2003/0203507 | A1 | * | 10/2003 | Liberti et al. | 436/526 |

\* cited by examiner

Primary Examiner—Bhavesh M. Mehta
Assistant Examiner—Barry Choobin
(74) Attorney, Agent, or Firm—G.E. Ehrlich (1995) Ltd.

(57) ABSTRACT

A system for generating a profile of particulate components of a body fluid sample is provided. The system includes: (a) a device for causing controlled flow of the body fluid sample on a substrate, the controlled flow of the body fluid sample leading to a differential distribution of the particulate components on the substrate; and (b) a magnifying device being for providing a magnified image of differentially distributed particulate components on the substrate, the magnified image representing a profile of the particulate components of the body fluid sample.

32 Claims, 21 Drawing Sheets

(20 of 21 Drawing Sheet(s) Filed in Color)

Fig. 11a        Fig. 11b        Fig. 11c        Fig. 11d
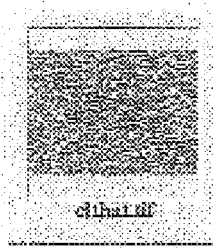 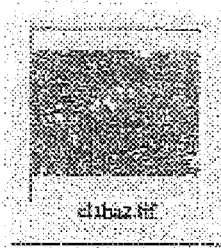 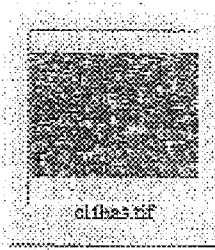 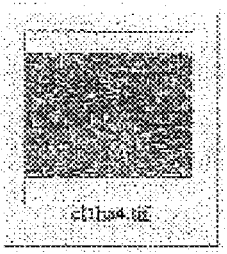
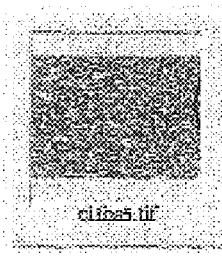 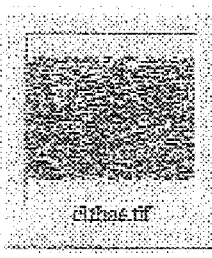 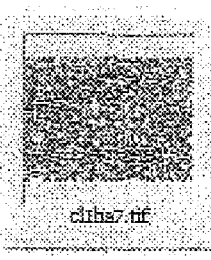 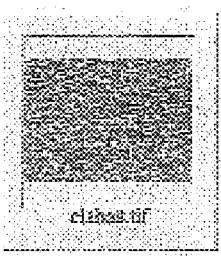
Fig. 11e        Fig. 11f        Fig. 11g        Fig. 11h
Control
Fig. 11i        Fig. 11j        Fig. 11k        Fig. 11l
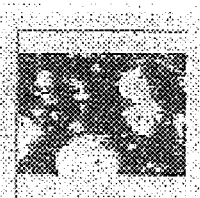 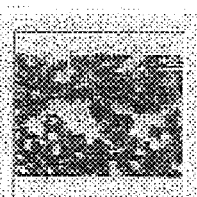 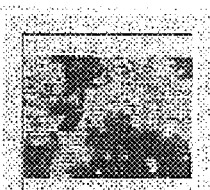 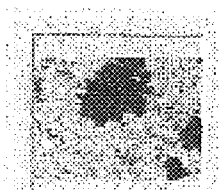
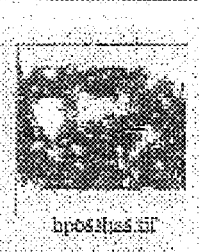 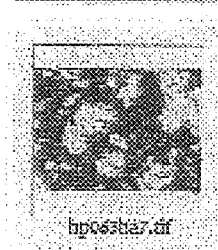 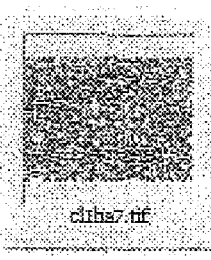 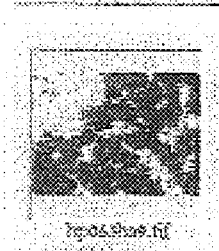
Fig. 11m        Fig. 11n        Fig. 11o        Fig. 11p
Patient Fig. 12a  Fig. 12b  Fig. 12c  Fig. 12d
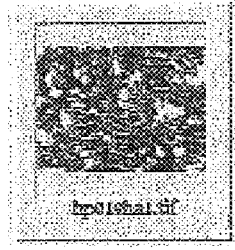 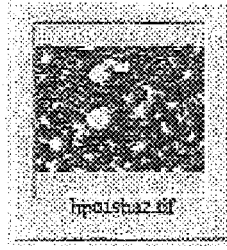 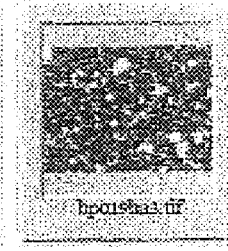 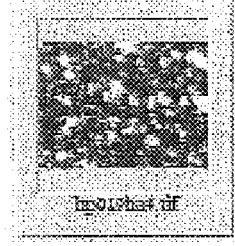
Fig. 12e  Fig. 12f  Fig. 12g  Fig. 12h
Bacterial
Fig. 12i  Fig. 12j  Fig. 12k  Fig. 12l
 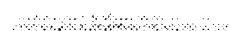 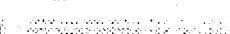 
Fig. 12m  Fig. 12n  Fig. 12o  Fig. 12p
Viral Examples of Control Samples EP = 85%
AR = 50.6 micron
VR = 0.7 micron
RC = N/A
PP = N/A
Leukocytes per square mm: 213
13% in clusters
WBC: [ 4.1 13.3]
LEP = N/A Examples of Control Samples Erythrocyte Aggregation
EP = 69%
AR = 25.1 micron
VR = 2.7 micron
Leukocytes per square mm: 306
WBC: [ 5.9  19.1]
15% in clusters Examples of Control Samples Erythrocyte Aggregation
EP = 29%
AR =   14.9 micron
VR =   37.1 micron
RC =   7.3 micron
PP =   33
Leukocytes per square mm: 852
75% in clusters
WBC: 1   16.4   53.31

SYSTEM AND METHOD FOR GENERATING A PROFILE OF PARTICULATE COMPONENTS OF A BODY FLUID SAMPLE

This is a continuation in part of PCT/IL00/00673 filed Oct. 23, 2000.

FIELD AND BACKGROUND OF THE INVENTION

The present invention relates to system and methods for generating a profile of particulate components of a body fluid sample. More particularly, embodiments of the present invention relate to a system and method which can be utilized to detect and diagnose an inflammatory condition in an individual.

Diagnosis of various clinical conditions is many times based on the determination of the presence and/or level of several components present in body fluids, mainly in the blood. Such body fluid evaluation provides information about the physiological and clinical state of an individual and can be indicative of the presence, absence and at times progression of an illness.

A widely accepted medical school doctrine teaches that the complete blood count including the white blood cell differential (CBC+Diff) is one of the best tests for assessing a patient's overall health. With it, a physician can detect or diagnose for example, anemia, infection, blood loss, acute and chronic diseases, allergies, and other conditions characterized by deviation from normal values and thus to identify the existence and assess the severity of the patient's condition in order to propose a future therapeutic approach. Moreover, CBC+Diff analysis provide comprehensive information on blood constituents, including the number of red blood cells, hematocrit, hemoglobin concentration, and on indices that portray the size, shape, and oxygen-carrying characteristics of the entire red blood cell (RBC) population. The CBC+Diff also includes the number and types of white blood cells and the number of platelets. Thus, CBC+Diff is one of the most frequently requested diagnostic tests with about two billion done in the United States per year.

One of the most common phenomena which accompany many disorders and diseases is the inflammatory response. Inflammation results from a complex of cellular and humoral events which arise as a response to many stimuli such as impact, distortion, chemical irritation, infection by pathogenic organisms (such as bacteria or viruses) or extreme temperatures. The development of an inflammatory response is accompanied by an acute phase response in which various kinds of proteins such as, for example, fibrinogen, haptoglobin, ceruloplasmin, ferritin and c-reactive proteins are synthesized. Typically, the most common parameters which are tested in order to diagnose inflammation in an individual are the total white blood cell (leukocytes) count (WBCC), red blood cell (erythrocytes) sedimentation rate (ESR) and quantitative C-reactive protein (CRP) which allow the discrimination between the presence or the absence of an inflammatory response.

Tests which are used to determine parameters associated with inflammation are typically carried out automatically by instruments such as automated counters, laser nephelometers or automatic ELISA readers, which are capable of counting and classifying different components of the body fluid sample on the basis of predefined characteristics (such as size, shape and concentration).

A main problem in such automated systems stems from the fact that the components of body fluid and in particular the cellular components are in fact dynamic components which interact with one another and thus their physical characteristics may not fall within the exact predefined characteristics of the automated instrument. Thus for example, many of the proteins synthesized during the acute phase response of an inflammation, cause the cells to aggregate with cells of the same type as well as with cells of other types. An aggregate comprised of several cells may be classified by the automated device as a large unclassified cell (LUC) while, in fact each of the cells comprising the aggregate should have been added to the specific cell population count to which they belong. The result of such an error in classification can, for instance, bring about an erroneous WBCC and thus to an erroneous diagnosis of pseudoleukopenia. In addition, it is also common that a WBCC result which is within normal limits is obtained by routinely used methods (mainly by electronic counters) while, in actuality, the WBCC is substantively higher. Such an erroneous "normal" WBCC may substantively influence the diagnostic decision of a physician and result in non-effective or even harmful treatment.

Furthermore, currently utilized methods for evaluating body fluids which utilize automated instruments require relatively large amounts of body fluid such as a blood sample in order to perform the evaluation. This may be problematic in cases where large volumes of the body fluid are not available for diagnosis, such as the case in newborns. This problem becomes even more severe in view of the fact that, in most cases, in order for a physician to diagnose a certain condition in an individual, it is necessary to carry out at least two separate tests, each requiring a separate sample. Typically, one test will be a total white blood cell count and often also a differential count in which white blood cells of each subpopulation (e.g. neutrophils, lymphocytes, etc.) are counted separately. The other test will typically be an erythrocyte sedimentation rate (ESR) test.

An additional drawback to presently used methods arises from the fact that due to the relatively large amounts of body fluids required for each diagnostic test, it is difficult to repeat the diagnostic test over short intervals of time. This drawback imposes severe limitations on diagnosis using such methods since test repetition is often required for monitoring the progression of a clinical condition over time.

It is known that white blood cells change their adherence properties and aggregation tendencies during inflammation since their membranes become more "sticky". A leukocyte adhesiveness/aggregation test (LAAT) based on the aggregation of cells in a body fluid to one another, was described previously as a tool for diagnosing the presence of an inflammatory response and assessment of its severity in various disorders and diseases. LAAT has also been proposed as a method of discriminating between bacterial infections (in which there is a high level of leukocyte aggregation) and viral infections (wherein attenuated or no leukocyte aggregation is detected). Aggregation of other types of cells such as erythrocytes and platelets has also been correlated to various conditions involving inflammation but these parameters have not been used for diagnosis of such conditions.

Another limitation inherent to presently utilized diagnostic systems arises from the fact that due to the complexity of tests and equipment involved, the use of such systems in telemedicine cannot be easily effected.

Telemedicine is the process of sending test data and/or images from one point to another through networks, typically over standard telephone lines, or over a wide-area network using dial-up ISDN lines or other switched digital services. Using telemedicine, images can be sent from one part of a hospital to another part of the same hospital, from one hospital to another, from remote sites to diagnostic centers, etc. In other words, test data and/or images obtained at one location can be sent to almost any place in the world.

As cost-effective diagnosis becomes a major issue, telemedicine is becoming an acceptable way to make diagnoses and to consult with referring physicians. Computer-assisted transfer of digitized images allows geographically dispersed consultants to lend their expertise to remote regions, thereby benefiting patients who now may have limited access to advanced medical services. Telemedicine systems are especially important in rural medical facilities, where skilled physicians or automated analysis systems are not available.

There is thus a widely recognized need for, and it would be highly advantageous to have, a system and method which can be utilized to manually or automatically analyze biological samples such as blood samples to thereby enable diagnosis of patient's clinical condition, while being easily implementable and utilizable in telemedical architecture.

SUMMARY OF THE INVENTION

According to one aspect of the present invention there is provided a system for generating a profile of particulate components of a body fluid sample comprising: (a) a device for causing controlled flow of the body fluid sample on a substrate, the controlled flow of the body fluid sample leading to a differential distribution of the particulate components on the substrate; and (b) a magnifying device being for providing a magnified image of differentially distributed particulate components on the substrate, the magnified image representing a profile of the particulate components of the body fluid sample.

According to further features in preferred embodiments of the invention described below, the system further comprising an imaging device being for capturing the magnified image provided by the magnifying device.

According to still further features in the described preferred embodiments the imaging device is a camera.

According to still further features in the described preferred embodiments the system farther comprising an image analyzer being in communication with the imaging device, the image analyzer being configured for analyzing the profile of the particulate components in the body fluid sample.

According to still further features in the described preferred embodiments the image analyzer communicates with a display for displaying the magnified image.

According to still further features in the described preferred embodiments the image analyzer communicates with a printer for providing a printed output including the magnified image and/or data of an analyzed profile.

According to still further features in the described preferred embodiments the communication between the image analyzer and the imaging device is effected through a communication network.

According to still further features in the described preferred embodiments the communication between the image analyzer and the imaging device is effected through at least one communication server.

According to another aspect of the present invention there is provided a system for generating a profile of particulate components of a body fluid sample comprising: (a) at least one apparatus for generating a profile of the particulate components of the body fluid sample, the at least one apparatus including: (i) a device for causing controlled flow of the body fluid sample on a substrate, the controlled flow of the body fluid sample leading to a differential distribution of the particulate components on the substrate; and (ii) a magnifying device being for providing a magnified image of differentially distributed particulate components on the substrate, the magnified image representing a profile of the particulate components of the body fluid sample, and (iii) an imaging device being for capturing the magnified image provided by the magnifying device; (b) an image analyzer being in communication with the at least one apparatus, the image analyzer being configured for analyzing the profile of the particulate components in the body fluid sample; and (c) at least one communication server being for communicating the magnified image from the at least one apparatus to the image analyzer.

According to still further features in the described preferred embodiments the at least one communication server forms a part of the World Wide Web.

According to still further features in the described preferred embodiments the magnifying device is a light microscope, a camera with magnification capabilities or any general optical arrangement designed for magnification.

According to still further features in the described preferred embodiments the light microscope is selected from the group consisting of an inverted light microscope, a confocal microscope, and a phase microscope.

According to still further features in the described preferred embodiments the body fluid sample is a peripheral blood sample.

According to still further features in the described preferred embodiments the particulate components in the body fluid sample are selected from the group consisting of white blood cells, red blood cells, platelets, bacteria, hemoglobin, and plasma proteins.

According to still further features in the described preferred embodiments the profile of the particulate components in the body fluid sample is determined according to the differential distribution of the particulate components along at least one axis selected from the group consisting of an axis along a length of the substrate, an axis along a width of the substrate and an axis perpendicular to the substrate.

According to still further features in the described preferred embodiments the profile of the particulate components in the body fluid sample is characterizable according to at least one parameter selected from the group consisting of estimated hemoglobin concentration, approximated leukocyte count and differential, approximated platelet count, degree of leukocyte aggregation, aggregate composition, degree of leukocyte, erythrocyte and/or platelet adherence towards the surface of said substrate, degree of red cell aggregation, degree of platelet aggregation, degree of leukocyte to erythrocyte interaction, degree of erythrocyte to platelet interaction and degree of leukocyte to platelet interaction.

According to still further features in the described preferred embodiments the substrate is a slide, such as a glass slide.

According to still further features in the described preferred embodiments the substrate is coated with a molecule capable of binding a specific components of the particulate components.

According to still further features in the described preferred embodiments the substrate is coated with at least two specific types of molecules each being capable of binding a specific components of the particulate components.

According to still further features in the described preferred embodiments the device for causing controlled flow of the body fluid sample on a substrate is a holder capable of holding the substrate in an essentially angled position.

According to still further features in the described preferred embodiments the device for causing controlled flow of the body fluid sample on a substrate is a centrifuge.

According to still further features in the described preferred embodiments the imaging device converts the captured image into data communicable by the at least one communication server.

According to still further features in the described preferred embodiments the image analyzer includes a processing unit executing a software application designed and configured for analyzing and optionally characterizing the profile of the particulate components of the body fluid sample according to at least one parameter selected from the group consisting of estimated hemoglobin concentration, approximated leukocyte count and differential, approximated platelet count, degree of leukocyte aggregation, aggregate composition, degree of leukocyte, erythrocyte and/or platelet adherence towards the surface of said substrate, degree of red cell aggregation, degree of platelet aggregation, degree of leukocyte to erythrocyte interaction, degree of erythrocyte to platelet interaction and degree of leukocyte to platelet interaction.

According to yet another aspect of the present invention there is provided a method of generating a profile of particulate components in a body fluid sample comprising the steps of: (a) causing controlled flow of the body fluid sample on a substrate, the controlled flow of the body fluid sample leading to a differential distribution of the particulate components on the substrate; and (b) providing a magnified image of differentially distributed particulate components on the substrate, the magnified image representing a profile of the particulate components in the body fluid sample.

According to still another aspect of the present invention there is provided a method of determining an atherosclerosis risk factor of an individual, the method comprising the steps of: (a) causing controlled flow of a body fluid sample obtained from the individual on a substrate, the controlled flow of the body fluid sample leading to a differential distribution of particulate components included in the body fluid sample on the substrate; (b) providing a magnified image of differentially distributed particulate components on the substrate, the magnified image representing a profile of the particulate components in the body fluid sample; (c) analyzing at least one parameter of the profile to thereby determine the atherosclerosis risk factor of the individual.

According to still further features in the described preferred embodiments the method further comprising the step of analyzing and optionally characterizing the profile representing the particulate components in the body fluid sample according to at least one parameter selected from the group consisting of estimated hemoglobin concentration, approximated leukocyte count and differential, approximated platelet count, degree of leukocyte aggregation, aggregate composition, degree of leukocyte, erythrocyte and/or platelet adherence towards the surface of said substrate, degree of red cell aggregation, degree of platelet aggregation, degree of leukocyte to erythrocyte interaction, degree of erythrocyte to platelet interaction and degree of leukocyte to platelet interaction.

According to still further features in the described preferred embodiments the step of analyzing and optionally characterizing the profile representing the particulate components in the body fluid sample is used for determining a presence or absence of, a clinical condition in an individual.

According to still further features in the described preferred embodiments the step of analyzing and optionally characterizing the profile representing the particulate components in the body fluid sample is used for determining the efficiency of a treatment regimen.

According to still further features in the described preferred embodiments the step of analyzing and optionally characterizing the profile representing the particulate components in the body fluid sample is used for diagnosing a disorder in an individual.

According to still further features in the described preferred embodiments the method further comprising the step of staining the particulate components prior to step (b).

According to still further features in the described preferred embodiments the clinical condition is caused by an agent selected from the group consisting of an infective agent and a chemical agent.

According to still further features in the described preferred embodiments the clinical condition is caused by a disorder selected from the group consisting of atherosclerosis, diabetes, viral infection and bacterial infection.

According to still further features in the described preferred embodiments the method further comprising the step of converting the magnified image into data prior to the step of analyzing.

According to still further features in the described preferred embodiments the body fluid sample is a peripheral blood sample.

According to still further features in the described preferred embodiments the step of causing controlled flow of the body fluid sample on a substrate is effected by a holder capable of holding the substrate in an essentially angled position, or by a centrifuge.

According to still further features in the described preferred embodiments the at least o n e parameter is selected from the group consisting of a number of white blood cells, leukocytes adhesiveness/aggregation state (LAAT), erythrocytes adhesiveness/aggregation state (EAAT), increased fibrinogen concentrations, concentration of C-reactive protein (CRP), hyperlipidemia, and erythrocytes sedimentation rate (ESR).

According to yet another aspect of the present invention there is provided a method of generating a profile of a body fluid sample comprising the steps of: (a) causing controlled flow of the body fluid sample on a substrate, the controlled flow of the body fluid sample leading to a distribution of the body fluid sample on the substrate; and (b) determining a thickness variance of the body fluid sample along a direction of the controlled flow on the substrate, the thickness variance representing a profile of the body fluid sample.

According to still further features in the described preferred embodiments the method further comprising the step of analyzing and optionally characterizing particulate components of the body fluid sample in at least one specific region of the substrate.

According to still further features in the described preferred embodiments the profile of the body fluid sample is used for determining a presence or absence of a clinical condition in an individual.

According to still further features in the described preferred embodiments the step of analyzing and optionally characterizing particulate components of the body fluid sample in the at least one specific region of the substrate is used for diagnosing a disorder in an individual.

According to still another aspect of the present invention there is provided a carrier comprising a plurality of lanes each occupying a length and a portion of a width of a surface of the carrier, each lane of the plurality of lanes being coated with a specific molecule capable of binding a specific cell type present in a biological sample.

According to still further features in the described preferred embodiments the carrier is designed and configured for placement in a microscope stage.

The present invention successfully addresses the shortcomings of the presently known configurations by providing a system and methods for generating a profile of particulate components of a body fluid sample. More particularly, embodiments of the present invention relate to a system and method which can be utilized to detect and diagnose an inflammatory response in an individual.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a black box diagram of an "on-site" system for generating and evaluating a profile of particulate components of a body fluid sample according to the teachings of the present invention.

FIG. 2 is a black box diagram of a "remote" system for generating and evaluating a profile of particulate components of a body fluid sample according to the teachings of the present invention.

FIG. 3 is a photograph of a blood sample obtained according to the teachings of the present invention illustrating red cell aggregation (arrows) in a patient with accelerated erythrocyte sedimentation rate;

FIG. 4 is a photograph of a control blood sample obtained according to the teachings of the present invention showing that most of the red blood cells are in a non-aggregated state.

FIG. 5 is a photograph of a blood sample obtained according to the teachings of the present invention illustrating separation of white blood cells from the red blood cells.

FIG. 6 is a photograph of a blood sample obtained according to the teachings of the present invention illustrating leukocyte-erythrocyte interactions.

FIG. 7 is a photograph of a blood sample obtained according to the teachings of the present invention illustrating platelet aggregation (arrows) detectable in the peripheral blood during inflammation.

FIG. 8 is a photograph of a blood sample obtained according to the teachings of the present invention illustrating leukocyte-platelet interactions (arrow) which are observed during an inflammatory response characterized by cellular activation.

FIG. 9 is a photograph of a blood sample obtained according to the teachings of the present invention illustrating massive leukocyte aggregation in a patient with a severe inflammatory response.

FIGS. 10a–d are photographs of a blood sample obtained according to the teachings of the present invention. Each photograph illustrates leukocytes and platelets "entrapped" in protein rich areas (A or a) in a patient with an inflammatory response. Areas with no proteinaceous material (B or b) have very little or no cellular elements.

FIGS. 11a–p are images obtained according to the teachings of the present invention. Each image shows a different field of view (FOV) of a slide prepared from a blood sample. FIGS. 11a–h represent FOVs of a sample obtained from a control individual while FIGS. 11i–p represent FOVs of a slide prepared from a sample obtained from a patient suffering from sepsis.

FIGS. 12a–p are images of FOVs obtained from slides prepared by using the system of the present invention. FIGS. 12a–h are FOVs from samples obtained from a person suffering from a bacterial infection while FIGS. 12i–p are FOVs of a sample obtained from individuals suffering from a viral infection.

Figure 13:
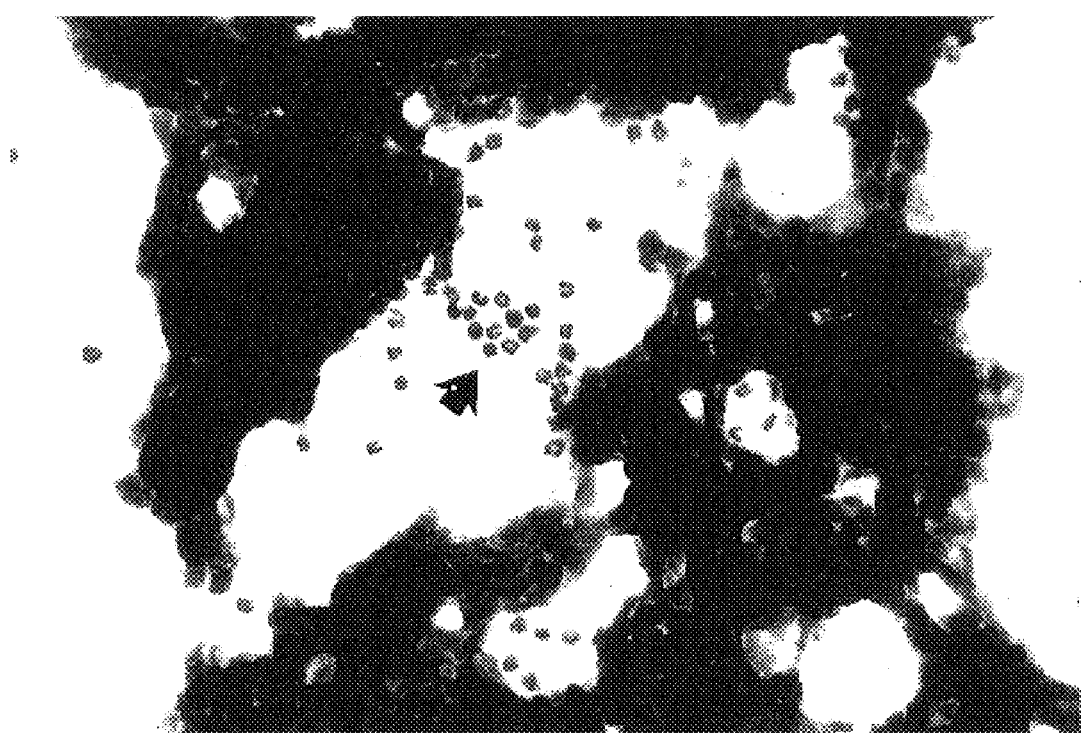

FIG. 13 is a photograph of a blood sample which was obtained according to the teachings of the present invention showing a significant inflammatory response including leukocytes, erythrocytes and platelet aggregation.

Figure 14:
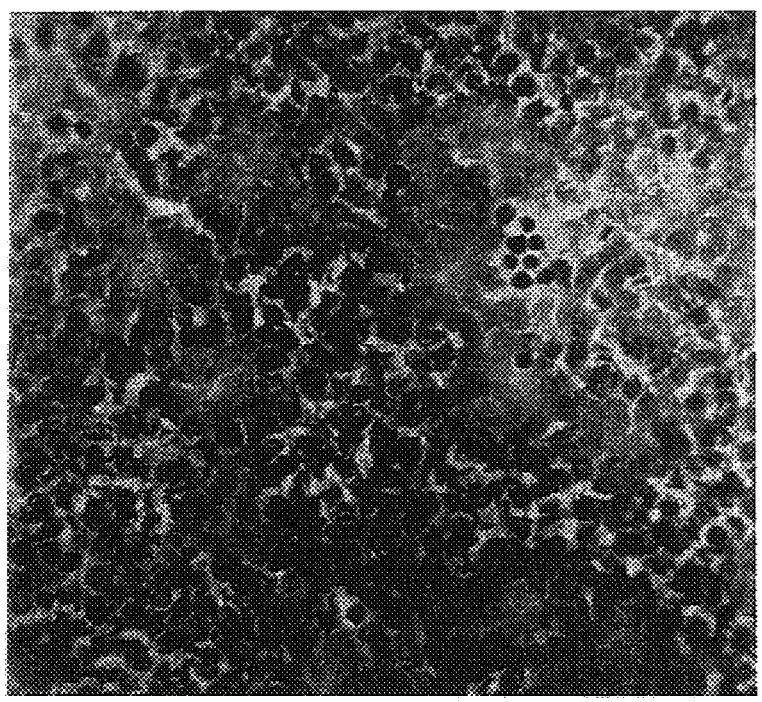

FIG. 14 is a photograph of a blood sample which was obtained according to the teachings of the present invention showing aggregation of lymphomononuclear leukocytes indicative of a viral infection with no acute phase response.

Figure 15A:
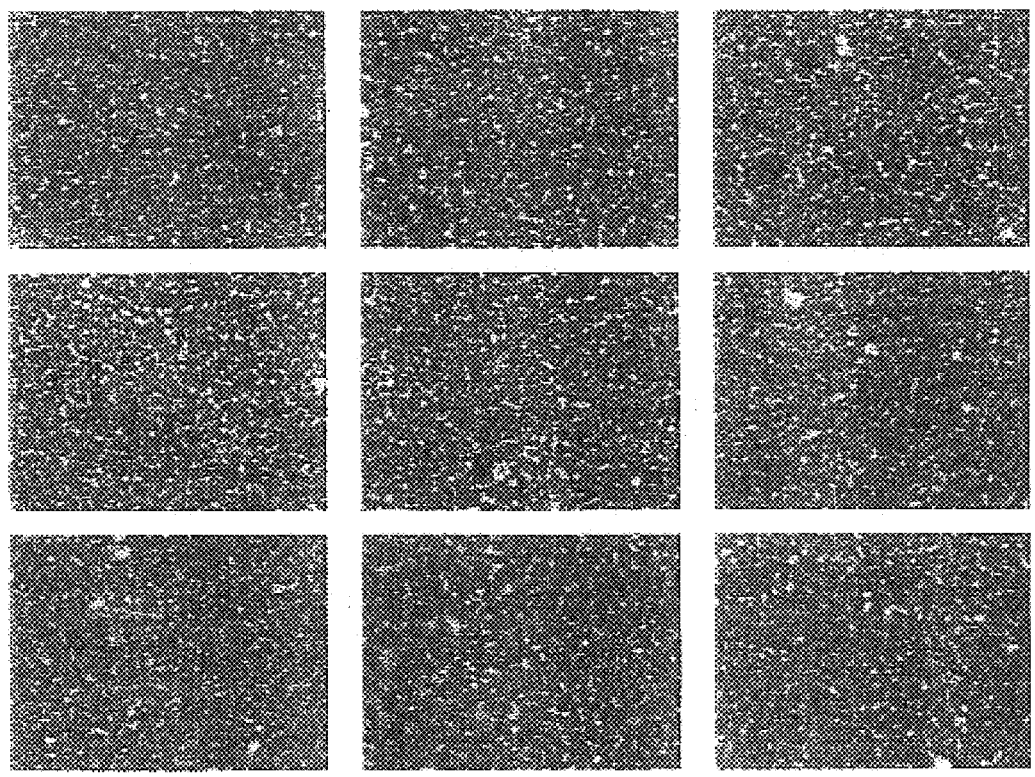
Figure 15A:
Figure 15A:
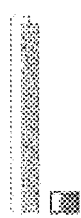
Figure 15B:
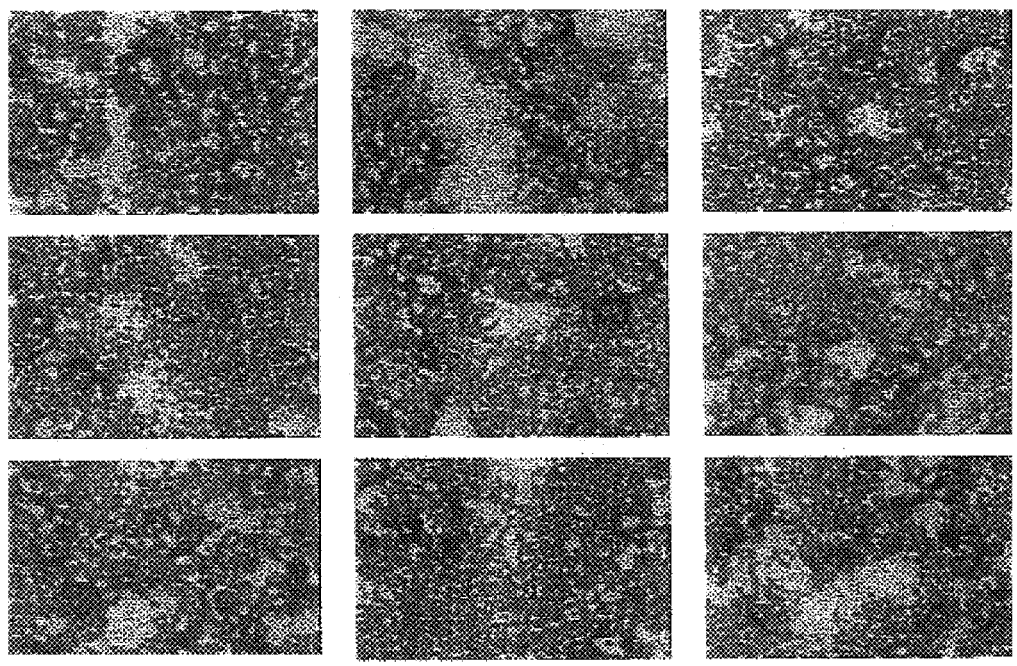
Figure 15B:
Figure 15B:
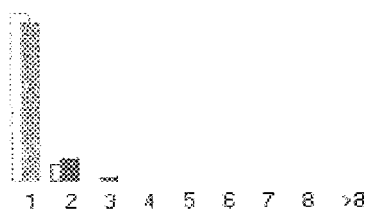
Figure 15C:
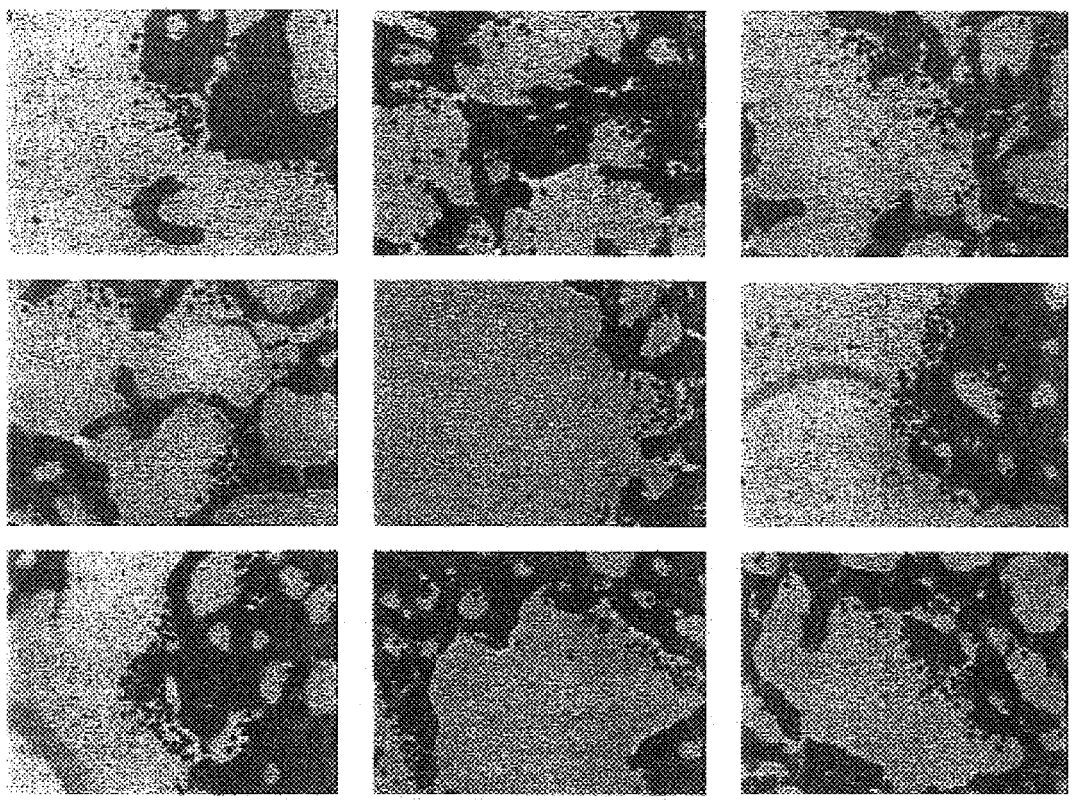
Figure 15C:
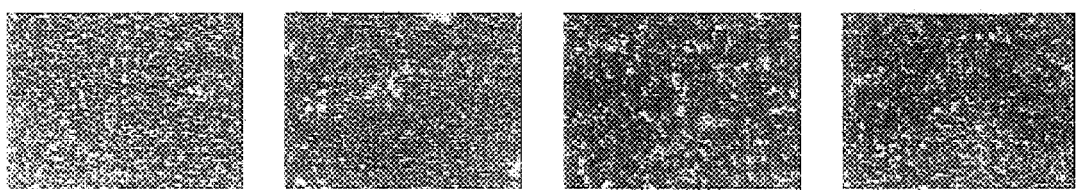
Figure 15C:
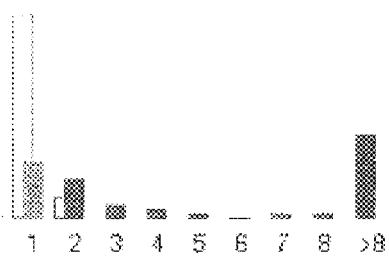

FIGS. 15a–c are images obtained by the system of the present invention from an individual suffering from a mild inflammation (FIG. 15a), an individual suffering from a moderate inflammation (FIG. 15b) and an individual suffering from a severe inflammation (FIG. 15c).

Figure 16:
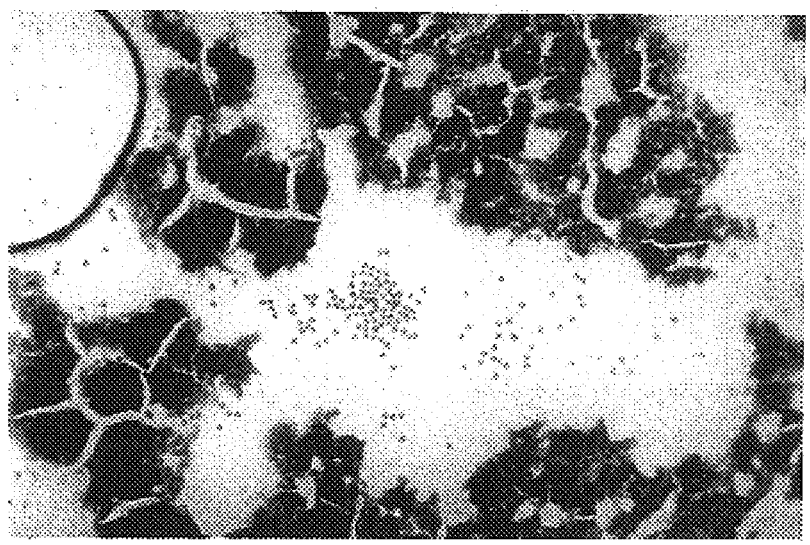

FIG. 16 is a photograph of a blood sample which was obtained from a child suffering from acute inflammation according to the teachings of the present invention. An abundant number of leukocytes and increased cellular aggregation which are indicative of inflammation can be clearly seen.

Figure 17A:
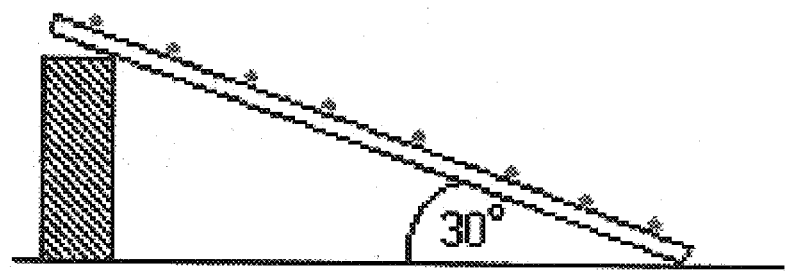
Figure 17B:
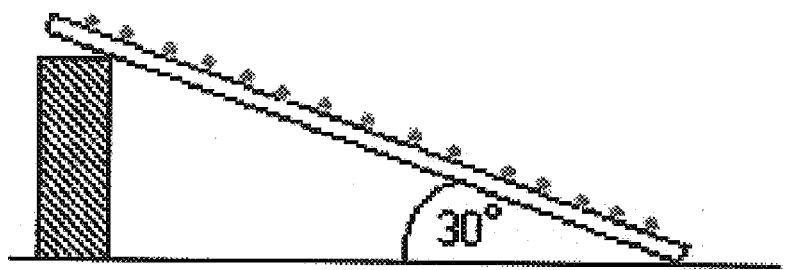

FIGS. 17a–b illustrate distribution of a particular cell component of a biological sample on an angled slide covered with an antibody not specific for the particular cell component (FIG. 17a) and specific for the particular cell component (FIG. 17b).

Figure 18:
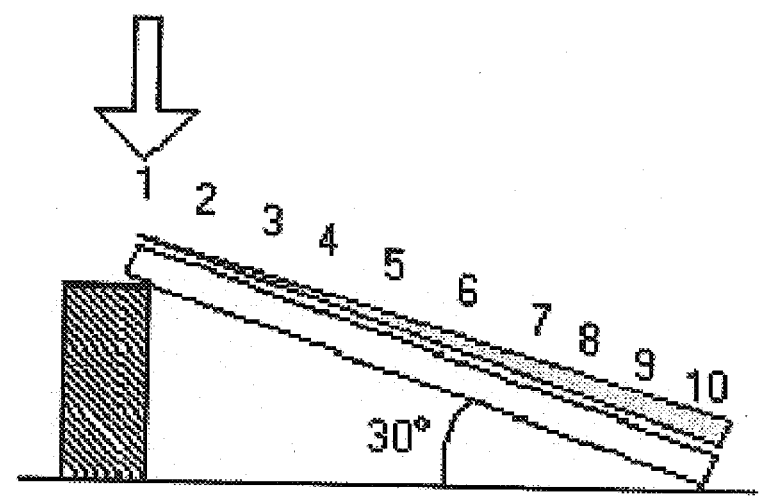

FIG. 18 illustrates thickness variance distribution of a blood sample on an angled slide carrier.

Figure 19:
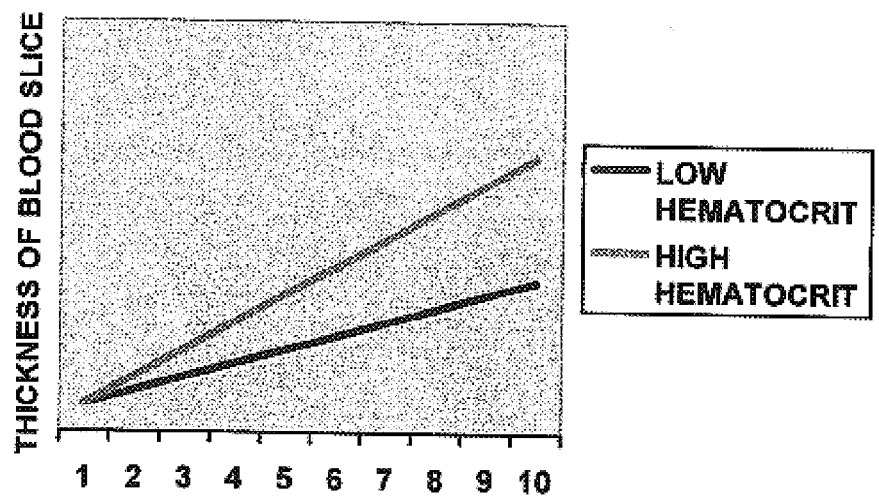

FIG. 19 is a graph illustrating the thickness of a distributed blood sample at various points along the angled slide shown in FIG. 18.

Figure 20A:
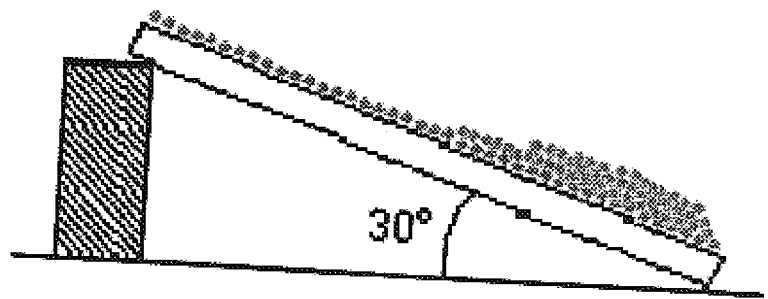
Figure 20B:
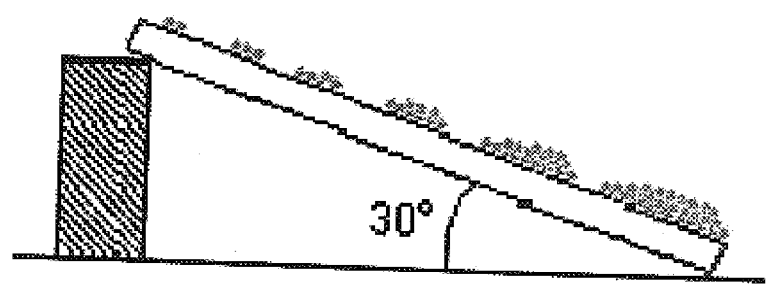

FIGS. 20a–b illustrates thickness variation in a normal blood sample (FIG. 20a) and a blood sample which is characterized by intercellular interactions typical of an inflammatory response.

Figure 21A:
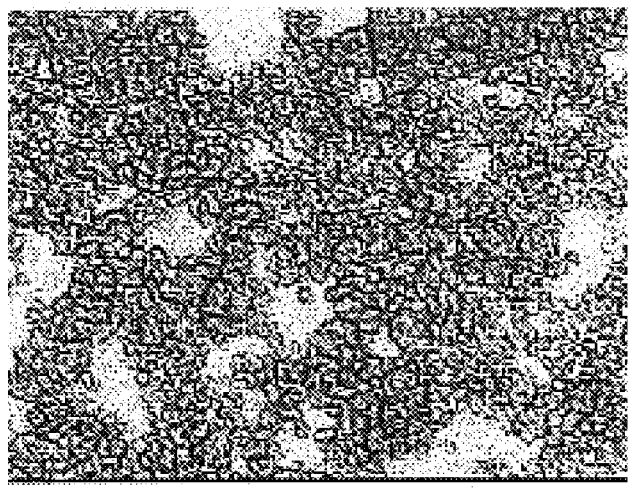
Figure 21B:
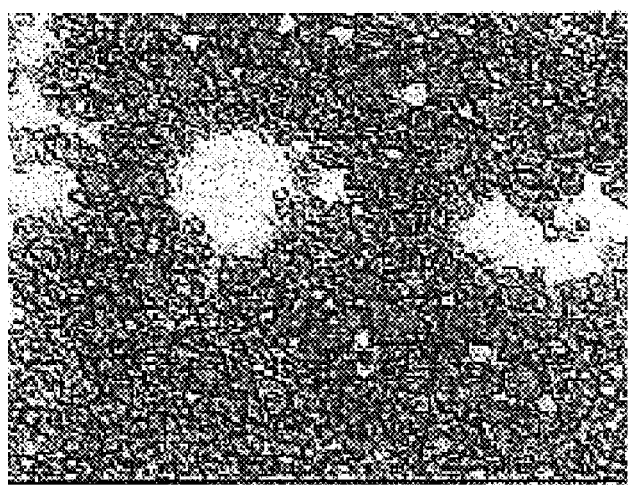
Figure 21C:
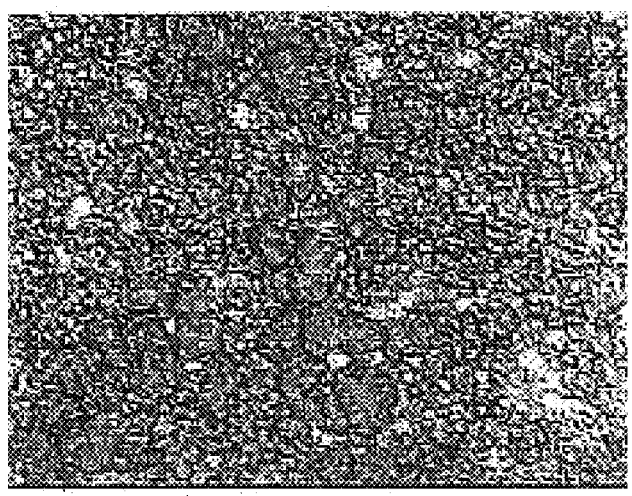

FIGS. 21a–c illustrate images taken of the upper (FIG. 21a), middle (FIG. 21b) and lower (FIG. 21c) portions of an angled slide.

Figure 22A:
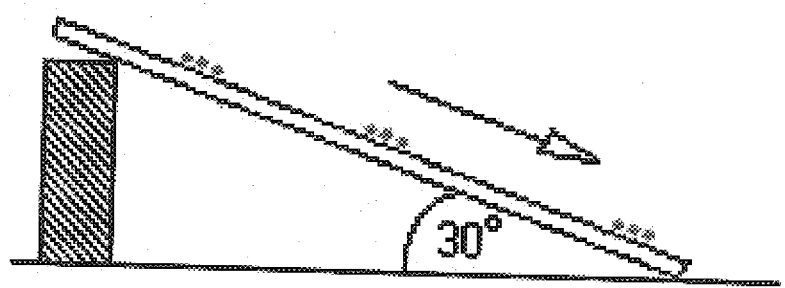
Figure 22B:
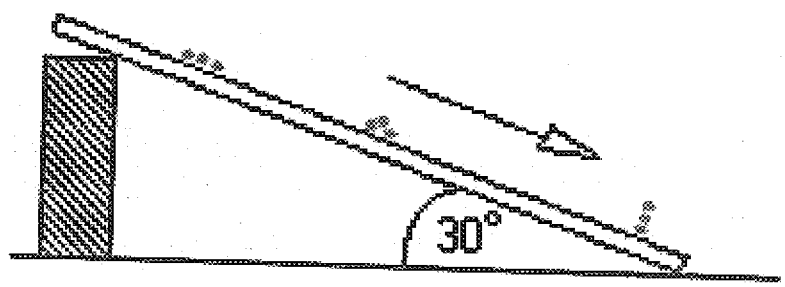

FIGS. 22a–b illustrate distribution of cellular components along an angled slide, in he case of weak intercellular interactions (FIG. 22a) and strong intercellular interactions (FIG. 22b).

DESCRIPTION OF THE PREFERRED EMBODIMENTS

The present invention is of a system and methods for generating a profile of particulate components of a body fluid sample, which profile can be utilized to detect and diagnose a clinical condition, such as, for example, an inflammatory response in an individual.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Currently utilized methods for evaluating body fluids which use automated instruments require relatively large amounts of body fluid such as a blood sample in order to perform an accurate diagnosis. This drawback imposes severe limitations since test repetition is often required for accurate diagnosis or for monitoring the progression of a clinical condition over time.

As The present invention provides a novel approach for analyzing biological samples of minimal volume to thereby enable accurate diagnosis of a variety of disorders and conditions using on-site as well as remote diagnosis configurations.

As used herein, the term "profile" refers to a magnified image of a body fluid sample which is representative of such a sample and which provides an initial indication of an individual's clinical condition.

As used herein, the phrase "body fluid" refers to a fluid sample obtained from a tested individual. Preferably, the body fluid sample is a blood sample obtained by standard techniques such as, a finger prick, or venous drawing. Other body fluids utilizable by the present invention are urine, saliva, lymph fluid, milk, cerebrospinal fluid, etc.

As used herein, the phrase "particulate components" refers to cellular and non cellular components of a body fluid, including, but not limited to, blood cells, platelets, proteinaceous material, such as hemoglobin and the like.

Figure 1:
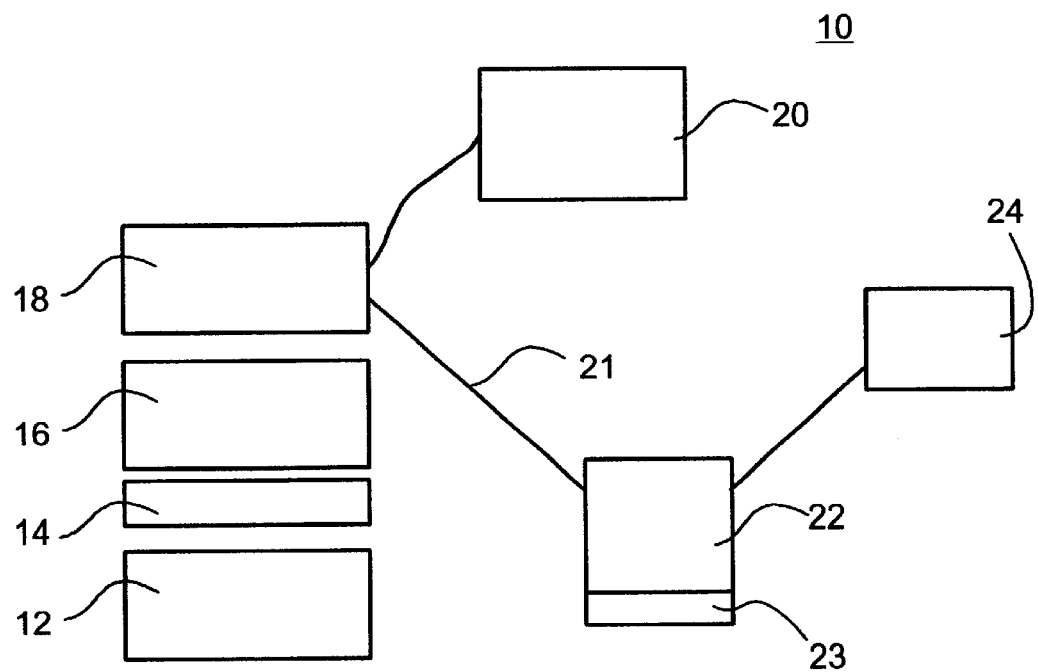

Referring now to the drawings, FIG. 1 illustrates one possible configuration of the system for generating a profile of particulate components of a body fluid sample, which is referred to hereinunder as system 10.

System 10 includes a device 12 which serves for causing a controlled flow of a body fluid sample when placed on a substrate 14 which is detachably attached to device 12. Substrate 14 can be any solid support onto which the body fluid sample is placed following collection and optionally processing. Examples include, but are not limited to, a glass or a plastic sample carrier (e.g. slide) which are optionally pretreated with, for example, antibodies or chemicals capable of modifying the surface property of the carrier.

According to one preferred embodiment of the present invention, device 12 is a holder which is capable of holding substrate 14 in an essentially angled position so as to allow controlled flow of the body fluid sample under the force of gravity for any predetermined time period.

According to another preferred embodiment of the present invention, device 12 is a centrifuge, such as for example a clinical centrifuge which is capable of exerting a centrifugal force on the body fluid sample placed on substrate 14.

In any case, when subjected to a gravitational or centrifugational force for a predetermined time period, a tested body fluid sample flows in the direction of the force. During this movement, each particulate component of the body fluid sample adheres to substrate 14 at a position which is dependent on the size, aggregation tendencies as well as adherence properties of the component. In general, smaller aggregates or components tend to move a greater distance on substrate 14 then larger aggregates or components.

As is further described in the Examples section which follows, this differential distribution of the particulate components on substrate 14 which is generated by device 12, represents a profile of particulate components of the body fluid sample.

To enable viewing of the profile generated, system 10 further includes a magnifying device 18. Magnifying device 18 can be a light microscope such as, for example, an inverted light microscope, a confocal microscope, or a phase microscope or any magnifying device capable of providing a magnified image of the differentially distributed particulate components.

It will be appreciated that although the above described configuration of system 10 is sufficient for enabling preliminary analysis of the profile of particulate components by a skilled operator, an imaging device which can capture and display the magnified image of the profile is preferably also utilized by system 10.

Thus, according to another preferred embodiment of the present invention, system 10 further includes an imaging device 18 which serves for capturing the magnified image provided by magnifying device 16. Imaging device 18 can be a camera, such as, a charged coupled device (CCD) camera, a scanner, a video camera, etc., or any other device capable of capturing an image of the profile of particulate components. Imaging device 18 may be wired to a display 20, such as a computer display, and/or a printer which serve for displaying and/or printing the magnified image captured by imaging device 18.

Captured and displayed and/or printed images provide an operator with a permanent and possibly enhanced record with which an initial evaluation of a patient condition can be effected. Additionally, captured images can provide an indication regarding the quality of the separation of the particulate components and also enable storage of collected data over a period of time.

It will be appreciated that although initial profile analysis can be extracted from such magnified images, especially when performed by an expert, additional information can be obtained from computerized image processing.

Such computerized analysis is effected according to predetermined processing parameters which are not dependent on the skill of the operator. As such, computerized processing can yield more accurate and reliable results especially when analyzing and comparing numerous samples from various patients.

Thus, according to another preferred embodiment of the present invention, system 10 further includes an image analyzer 22 which is in a direct or indirect communication with the imaging device 18 (as indicated by 21). Image analyzer 22 is designed and configured for analyzing the profile of the particulate components in the body fluid sample.

Preferably, image analyzer 22 includes a processing unit 23 which executes a software application or a collection of applications designed and configured for analyzing and optionally characterizing the profile of the particulate components of the body fluid sample (see the Examples section for further detail)

As is described in the Examples section which follows, such analysis is effected according to one or more parameters, each individually obtained from various FOVs (fields Of View) captured from the sample following processing by device 12. Depending on the parameter analyzed, the sample can be prestained to enhance general cellular features, specifically stained to enhance features such as for example, a cell surface or plasma protein (e.g. antibody staining) or left unstained.

Examples of parameters which can be evaluated include, but are not limited to, estimated hemoglobin concentration, approximated leukocyte count and differential, approximated platelet count, degree of leukocyte aggregation, aggregate composition, degree of leukocyte, erythrocyte and/or platelet adherence towards the surface of said substrate, degree of red cell aggregation, degree of platelet aggregation, degree of leukocyte to erythrocyte interaction, degree of erythrocyte to platelet interaction and/or degree of leukocyte to platelet interaction.

The present invention can also be used to provide additional parameters such as for example, the concentration of specific particulate components in a biological sample. For example, if a certain cell types of interest exhibits increased adhesive properties toward a certain type of protein, than a substrate (e.g., slide) coated with such a protein can be used to determine the presence or absence and/or concentration of such cell types in a biological sample.

In addition, the substrate can be coated (in a regiospecific manner) with more than one type of protein or interacting molecule to thereby generate a multi-track substrate which can be used to correlate the presence of several cell types. Specific examples of proteins which can be used as affinity coatings are given in Table 3 in the Examples section which follows.

Each of the above mentioned parameters can be analyzed and evaluated individually or in combination with other parameters in which case the effect of one parameter on another is also considered.

In any case, following analysis, each processed parameter or group of parameters is assigned a value which can be compared to value ranges (normal/abnormal) which are predetermined according to statistically processed data accumulated by system 10, or to data previously obtained by system 10 from the same patient.

Examples of parameter processing and evaluation and association of such processed parameters with various clinical conditions are given in the Examples section which follows (see for example, Table 2 therein).

To display analysis results, image analyzer 22 preferably also includes a display 24. Display 24 can so serve for displaying the magnified image so as to allow an operator to verify processed results. Display 24 can be for example, an LCD display a plasma display or a CRT display.

For example, an output which includes both numerical and image data can provide an operator with good and accurate indication of the clinical state of a patient.

Thus, system 10 of the present invention can provide a physician or operator thereof with processed data pertaining to the clinical condition of a patient. As is further described in the Examples section which follows, such a clinical condition can be indicative of a disorder, an infection or a trauma. For example, indications of an inflammatory response caused by acute bacterial or viral infection or by exposure to a chemical agent can be accurately detected by the system of the present invention by processing image data obtained from a processed blood sample of minimal volume (see Example 6 of the Examples section for further details).

The present invention can also be utilized to asses an atherosclerosis risk factor of an individual by evaluating one or more parameters including, but not limited to, leukocyte number, leukocytes adhesiveness/aggregation state (LAAT), erythrocytes adhesiveness/aggregation state (EAAT), as well as the platelet adhesiveness/aggregation test (PAAT).

The teachings of the present invention can also be used to generate a profile which relates to a variance in thickness of a substrate distributed biological sample. As is further described in Example 8 of the Examples section which follows, when a biological sample, such as a blood sample is placed on a slide and allowed to migrate downwards under the force of gravity for a predetermined time period, a sample distribution of varying thickness along the length of the slide is generated. Such variance in thickness along the path of migration represents a profile which can be correlated to various disorders and conditions (see Example 8 below for further detail).

It will be appreciated that profile related data which is acquired according to the teachings of the present invention, can be processed and/or evaluated either at the site of sampling (on-site analysis) or at a remote location (remote analysis) to provide diagnosis.

In an on-site configuration of system 10, sample processing, image capturing and parameter analysis can be effected by a single integrated device which includes the functions of devices 12, 16, 18 and image analyzer 22. It will be appreciated that in such an on-site configuration of system 10 a single computing platform having a single display can function in displaying the magnified image captured by imaging device 18, in processing such image data and in displaying the processed data to the operator.

Figure 2:
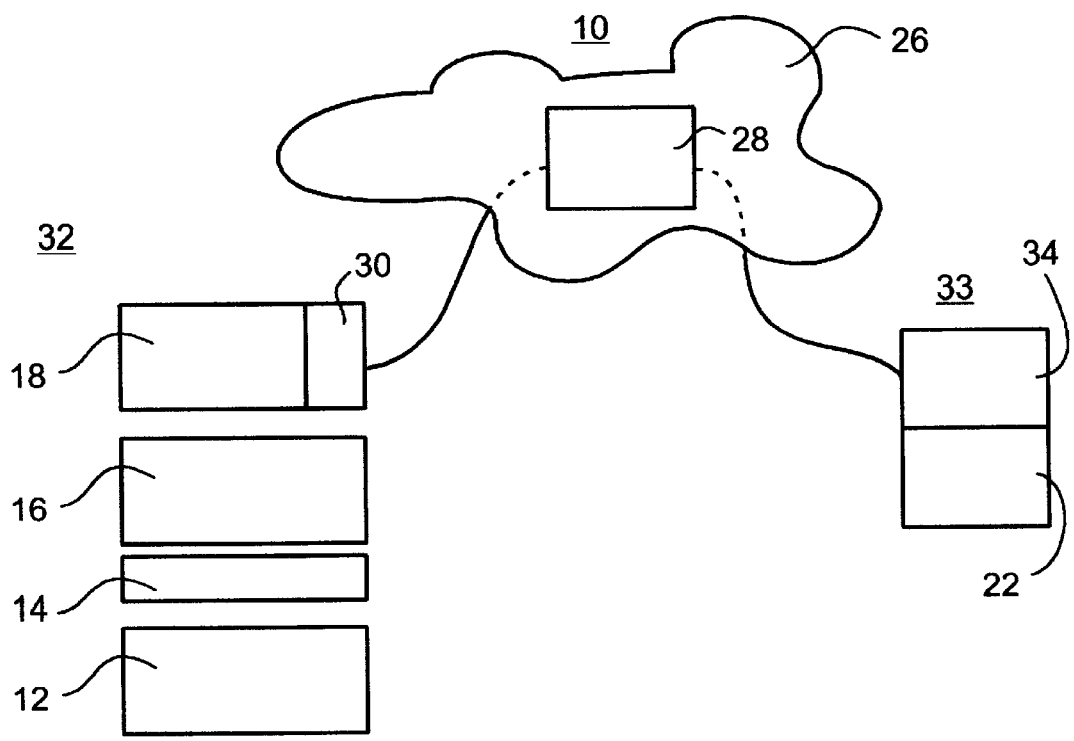

FIG. 2 illustrates a remote configuration of system 10 of the present invention.

In such a configuration, the communication between a remote image analyzer 22 and imaging device 18 is effected through a communication network 26. Communication network 26 can be any private or public communication network including, but not limited to, a standard or cellular telephony network, a computer network such as the Internet or intranet, a satellite network or any combination thereof.

As illustrated in FIG. 2, communication network 26 includes one or more communication servers 28 (one shown in FIG. 2) which serves for communicating data pertaining to the magnified image captured by at least one imaging device 18 from at least one sample processing location to remote image analyzer 22.

Thus, an image captured by imaging device 18 at a specific-sampling site 32 can be communicated via a dedicated computer terminal 30 to a remote analysis site 33, for analysis via image analyzer 22 and/or a skilled operator. Such communication can be effected via, e-mail communication, FTP transfer, direct Web-site upload or the like through, for example, a computer network such as the Internet. Preferably, the image data is compressed and optionally encoded prior to communication so as to enable rapid and accurate transmission. In addition, in order to avoid transmission errors, image data communicated from a sampling site 32 can be verified by remote analysis site 32 prior to analysis.

It will be appreciated that existing computer networks such as the Internet can provide the communication and applications necessary for supporting data communication between any number of sampling sites 32 and remote analysis sites 33.

For example, using the World Wide Web, image data collected at a sampling site can be "uploaded" onto a Web site maintained by a database server 34. Such an upload can be effected by a web browser program operated by computer terminal 30. Following uploading, the database server which serves as image analyzer 22 processes the image data as is described hereinabove.

Following analysis, which can be performed in real time, the results can be displayed at the web site maintained by database server 34 and/or communicated back to sampling site 32, via for example, e-mail communication.

As used herein, the term "Web browser" or "browser" refers to any software application which can display text, graphics, or both, from Web pages on World Wide Web sites. Examples of Web browsers include, Netscape navigator, Internet Explorer, Opera, iCab and the like.

Hereinafter, the term "Web site" is used to refer to at least one Web page, and preferably a plurality of Web pages, virtually connected to form a coherent group of interlinked documents.

Hereinafter, the term "Web page" refers to any document written in a mark-up language including, but not limited to, HTML (hypertext mark-up language) or VRML (virtual reality modeling language), dynamic HTML, XML (extended mark-up language) or related computer languages thereof, as well as to any collection of such documents reachable through one specific Internet address or at one specific World Wide Web site, or any document obtainable through a particular URL (Uniform Resource Locator).

Thus, using the Internet, a remote configuration of system 10 can provide image analysis services to a plurality of sampling sites 32 (one shown in FIG. 2). For example, each site 32, which can be, for example, a laboratory can maintain an account with database server 34 which account enables a laboratory technician to either submit image data for analysis or to perform analysis using analysis tools provided by database server 34. In addition, such an account could also enable restricted access to stored records and statistical data gathered and processed by database server 34.

Thus, the remote configuration of system 10 of the present invention functions as an application service provider (ASP) enabling the provision of diagnostic services to one or more sampling sites 32.

It will be appreciated that this configuration of system 10 of the present invention is especially advantageous in cases where diagnosis of samples can not be effected on-site. For example, laboratories which are situated in remote location or which lack the equipment necessary for analysis greatly benefit from telemedicine services providable by the remote analysis system of the present invention. In addition, the present invention may also be advantageous during research or space expeditions, or battle situations in which an accurate assessment of an individuals clinical condition which can not be performed otherwise is of great importance.

Thus, the system of the present invention can be utilized to evaluate a clinical condition in a patient either in an on-site or a remote configurations to thereby determine the presence or absence of a variety of disorders and conditions.

The present invention provides several distinct advantages over prior art diagnostic systems and methods. By enabling accurate diagnosis from a body fluid sample of minimal volume it enables diagnosis in infants or in individuals from which large volumes of blood cannot be drawn, thus traversing the limitations imposed upon prior art systems and methods. In addition, since it easily implementable in telemedicine practices, the provision of advanced diagnostic services to isolated locations or to location which lack the know how or equipment can be effected.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); "Cell Biology: A Laboratory Handbook", Volumes I–III Cellis, J. E., ed. (1994); "Culture of Animal Cells—A Manual of Basic Technique" by Freshney, Wiley-Liss, N.Y. (1994), Third Edition; "Current Protocols in Immunology" Volumes I–III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Generation of a Blood Sample Profile and Image for Particulate Components Evaluation The method of the present invention was compared to routinely used laboratory tests in the ability to predict the presence or absence of an inflammatory response.

As is further detailed hereinbelow, the method of the present invention is as accurate as routinely used laboratory tests such as, white blood cell count (WBCC), erythrocyte sedimentation rate (ESR) as well as quantitative C-reactive protein (CRP).

Blood Sample Preparation

Blood samples were prepared as previously described (Berliner, Fishelson, et al., 1987) with some modifications. Briefly, blood was drawn into a syringe which contained sodium citrate (one volume of 3.8% citrate and three volumes of peripheral blood). Several large drops of blood were placed on a glass slide which was held at an angle between 30°–45° for 2–3 seconds, allowing the blood drops to run down the slide, thus coating part of the slide with a fine film of blood. The slides were then dried in an incubator or at room temperature, while positioned at an angled or at a horizontal position. Manual hematoxylin staining was performed although any known automatic staining machines such as the HEMA TEK slide stainer (AMES) or HEMA TEK bloc colorant stain pack (Bayer Diagnostics) can also be utilized.

Obtaining an Optical Image

Several preselected fields of view (FOV) of the slide sample were obtained by a microscope. The FOVs may be manually or automatically selected and may be obtained at similar or different magnification levels. The magnification levels used are typically ×100, ×200 or ×400; a ×1,000 ocular is typically not used for the examination. Due to the relative thickness of the blood film on the glass substrate, not all the leukocytes were present at the same focal length and as such, the focal length had to be adjusted during the examination.

Preferably, imaging of the results is carried out using the INFLAMET™, image analysis system which consists of a Pentium computer running Windows 95, equipped with a Matrox Meteor color frame grabber [Berliner et al Int. J. Lab. Clin. Res. 30 (2000) 27–31] a color CCD camera and a microscope operating at a ×200 magnification thus resulting in an image resolution of 0.4 micron per pixel. Nine images which were chosen systematically to sample different regions on the slide and which covered a total area of 0.6 $mm^2$ were obtained and analyzed from each slide. Each image was processed separately and the outputs were then averaged to form a final output for each slide.

Example 2

Blood Cell Count and Differential

Acute phase response variables were analyzed by determining a white blood cell count and differential via the Coulter STKS electronic cell analyzer and by erythrocyte sedimentation which was performed as previously described (Westergren, International committee for standardization in hematology, Recommendation of measurement of erythrocyte sedimentation of human blood. 1965). Fibrinogen concentration was performed by using the method of Clauss (Clauss, 1957), and the Sysmex 6000 autoanalyzer, while the highly sensitive C-reactive protein concentrations (CRP) were determined by using the Dade Behring BN II nephelometer as described elsewhere (Rifai, Tracy et al 1999)

Example 3

Evaluation of an Optical Image of a Blood Sample Profile

Images obtained by the above procedure can be evaluated either manually or automatically as is further described hereinbelow.

Manual Image Characterization

The information obtained from the optical image provided by the system of the present invention, which represents a profile of the particulate components therein may be analyzed manually by a physician or a trained technician in order to evaluate the probability of the existence of an inflammatory reaction in the sample. This evaluation is based on the appearance of the various cellular components of the body fluid and the interactions between such components (for example adhesion and/or aggregation of various cell types). The information obtained from the optical instrument may also be transferred prior to, or following an initial analysis by a physician, to a computerized system capable of processing various qualitative and quantitative parameters of the particulate components of the body fluid sample.

Computerized Image Characterization

Several parameters can be identified and characterized via computerized image analysis. The number of white blood cells on a slide and the leukocyte adhesiveness/aggregation test (LAAT) can be assessed using the inflammation meter application software which detects white blood cells based on their color, shape and size characteristics and sorts them into clusters. Special attention is given so as to correctly detect and classify white blood cells even when they are in close proximity. For that purpose a special algorithm which rules out errors resulting in artifacts leukocyte merging and the like is utilized.

For the purpose of cluster analysis, two leukocytes were considered as being near to each other if the distance between their centers was less than 10 microns. The aggregation level of a slide was defined as the percentage of leukocytes in clusters of size >1.

The erythrocyte adhesiveness/aggregation test (EAAT) was utilized to determine the state of erythrocyte adhesiveness/aggregation in the peripheral blood. EAAT is determined by using the same image analysis system described above (INFLAMET™). The variable of erythrocyte aggregation used to describe the state of erythrocyte adhesiveness/aggregation is the vacuum radius (VR). Color characteristics are used to classify image pixels into two classes in order to define this variable. The two classes were as follows:

(i) Class 1: Aggregates of erythrocytes.
(ii) Class 2: Everything else (plasma, platelets, leukocytes).

A description of one-point and two-point statistics for this classification turned out to require very few parameters. The main reason for this is that the image statistics are homogenous (position-independent) and isotropic (direction-independent). The two-point statistics are described by the probability of assigning a pixel to class 1, given that it is a distance r from a pixel class 1, and, similarly, the probability of assigning a pixel to class 2, given that it is a distance r from a pixel of class 2. These probabilities are 1 for r=0 and they decrease as a function of r. The precise dependence of these probabilities on the inter-pixel distance r does not seem to convey biologically significant information. It was found that this is sufficient to calculate the distances for which the probability falls below a threshold which was fixed at 0.7 and labeled them the VR for class 2. This parameter, measured in microns, provide an idea of what is the typical size of erythrocyte aggregates and plasma "spaces".

Example 4

Results-manual Analysis

Images acquired according to the teachings of the present invention can be analyzed manually by a physician or a trained technician in order to evaluate the probability of the existence of an inflammatory reaction in the sample. Such an evaluation is based on the sample profile which is characterized by the appearance of various cellular components of the body fluid and the interactions between them.

Described below are examples of various images representing profiles of differentially distributed particulate components generated from blood samples of several different patients suffering from inflammation caused by variety of inflammatory stimuli. When analyzed manually, the images were communicated from a camera to a computer display so as to enable a physician to characterize and evaluate the patient clinical condition and to determine whether or not the patient is suffering from an inflammatory response.

Figure 3:

FIG. 3 represents red blood cell aggregation in a patient exhibiting an accelerated erythrocyte sedimentation rate. The inflammation meter permits a quantitative analysis of the degree of aggregation which is proportional to the sedimentation rate. Results were obtained on unstained slides within 10 minutes from blood drawing. The arrow indicates the aggregated red blood cells. This image analysis indicated that the patient from which the blood sample was taken is suffering from an inflammatory disease.

Figure 4:
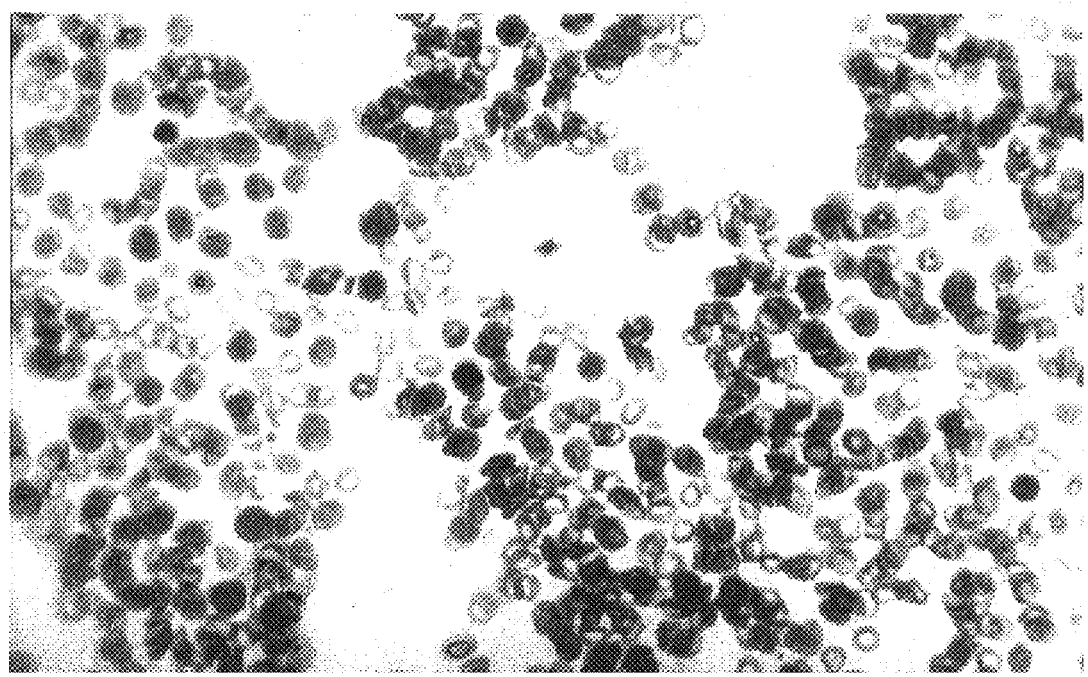

FIG. 4 represents an image of a control blood sample which was taken from a healthy individual. As seen therein, most of the red blood cells exist in a non-aggregated state. This precludes the presence of a significant acute phase response. The number of single red blood cells can be analyzed to exclude the presence of increased concentrations of "sticky" proteins, such as fibrinogen, fibronectin, haptoglobin, gamma globulins, and the like in the peripheral blood. It will be appreciated that the profile presented by such an image can be used to exclude the presence of the acute phase response with no need to measure the concentrations of such "sticky" proteins.

Figure 5:
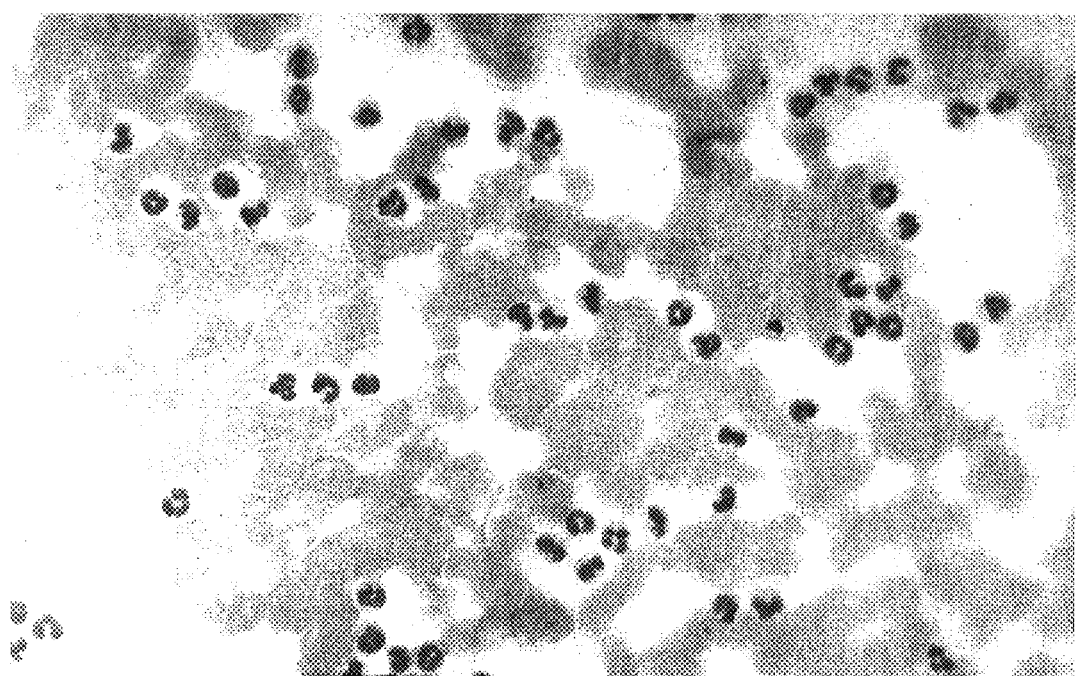

FIG. 5 illustrates an image acquired from a blood sample taken from an individual suffering from an inflammatory response which is characterized by a separation of white blood cells from the red blood cells. Such a situation results from the process of red cell aggregation. During the process of aggregation, leukocytes are "expelled" from the red blood cell mass formed. This separation is analogous to the formation of a "buffy coat" which is practically a separation of white cells from red blood cells. It is known that a spontaneous formation of a leukocyte rich plasma which occurs when a blood sample is kept in 1 G is proportional to the sedimentation rate and is enhanced during inflammation.

Figure 6:
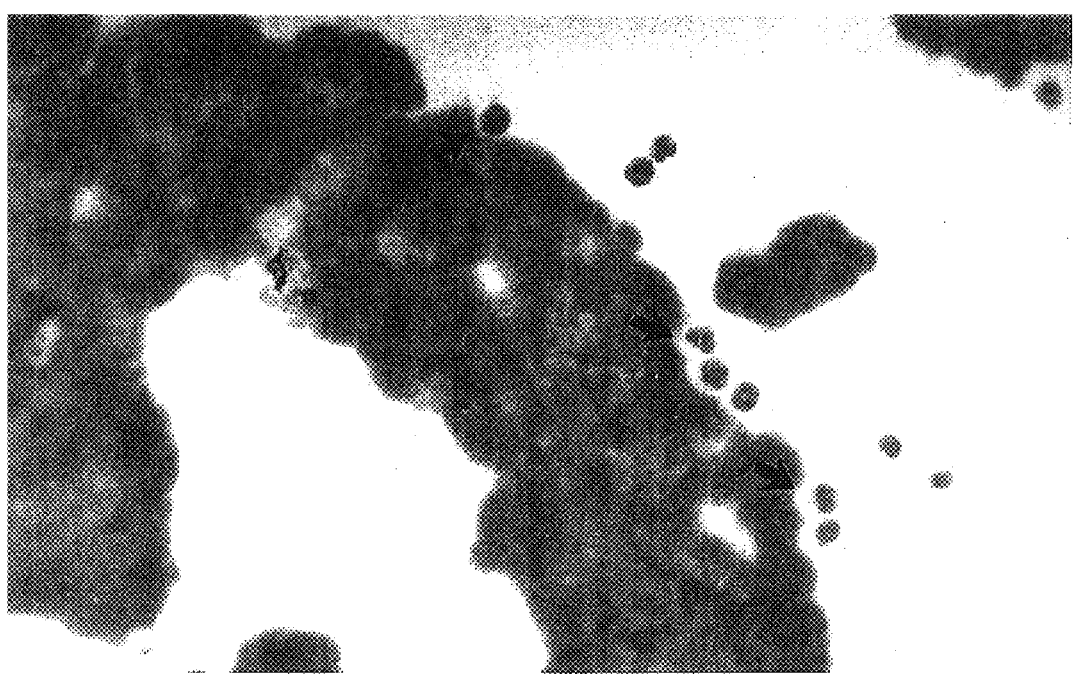

FIG. 6 is an image depicting a typical situation in which leukocytes and erythrocytes form close interactions. Such interactions are mediated by the sticky proteins which exist during an inflammatory response and as such are often indicative of an acute phase response. These interactions are clearly represented by FIG. 6 as special "pockets" which form when the surface of a red blood cell aggregate has adapted to the shape of the sojourning leukocyte. Such leukocyte-erythrocyte interactions are mediated by the "sticky proteins" which are present in the circulation and/or changes in the surface of the cells otherwise one cannot explain why there is no random distribution of the leukocyte cell over the slide.

Figure 7:
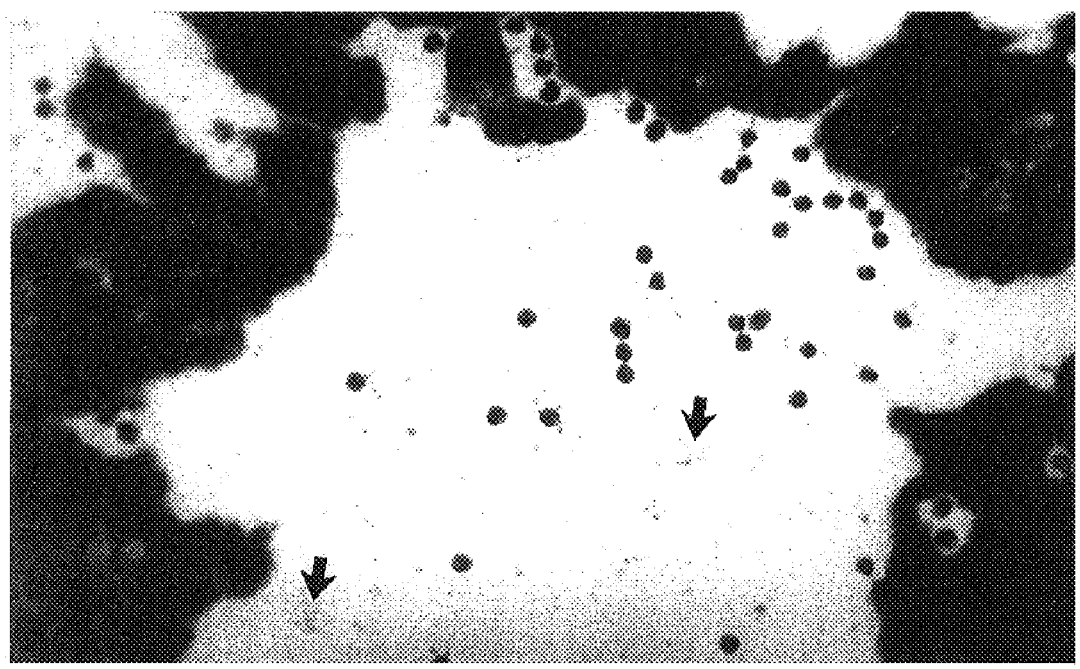

FIG. 7 is an image illustrating platelet aggregation (arrows) which can be detected in the peripheral blood of an individual suffering from an inflammation. Such a phenomenon is not seen in control patients. This aggregation which can be quantitated by the present invention, can serve as supporting evidence to an inflammatory response involving both acute phase protein synthesis and platelet activation.

Figure 8:
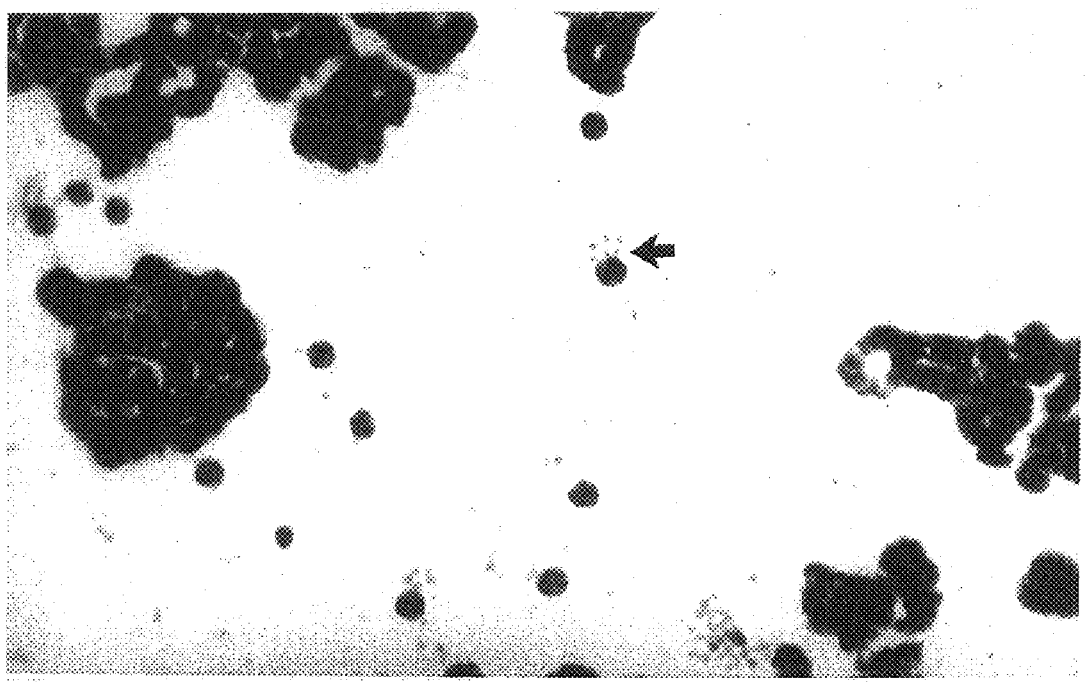

FIG. 8 illustrates leukocyte-platelet interaction (arrow) which is indicative of an inflammatory response marked by cellular activation determined using whole blood flow cytometry.

Figure 9:
Figure 10A:
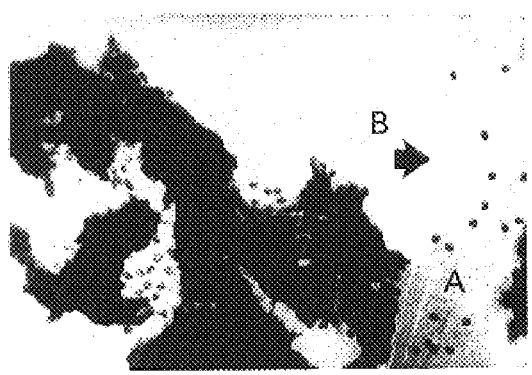
Figure 10B:
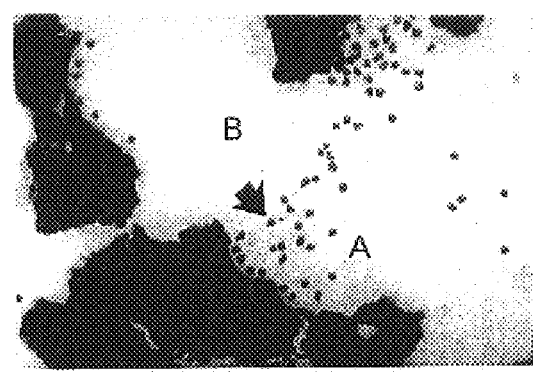
Figure 10C:
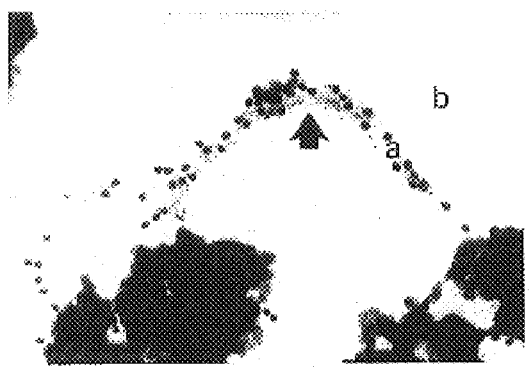
Figure 10D:
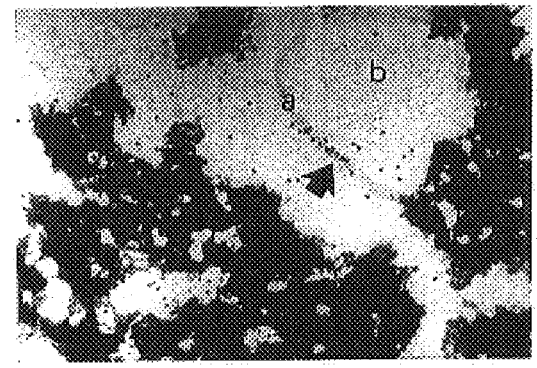

FIG. 9 illustrates a massive leukocyte aggregation in a blood sample taken from a patient suffering from a severe inflammatory response. In this case, the intensity of the inflammatory response can be correlated to the degree of leukocyte aggregation.

FIGS. 10a–d illustrate entrapment of white blood cells and platelets in proteinaceous rich areas (A) as compared to areas in which there is no proteinaceous material (B) where no cellular elements are seen. The above phenomena is seen only in patients with an acute phase response and not in samples from control individuals. Arrows indicate the border between the proteinaceous rich and poor areas.

FIGS. 11a–p represent fields of view (FOVs) of slides prepared using the system of the invention from samples of control non-inflamed individuals (upper eight pictures) as compared to a sample taken from an individual suffering from sepsis. The picture clearly shows that the sample taken from the patient suffering from inflammation is colored more extensively than the sample taken from the control non-inflamed individual due to the acute phase response in the inflamed individual resulting in increase in the level of proteins which absorb more color during the staining procedure.

FIGS. 12a–p represent FOVs obtained from two samples (obtained as explained in FIGS. 11a-p above). The eight upper pictures shows FOVs from a slide prepared from a sample taken from an individual suffering from a bacterial infection as compared to the lower eight pictures showing FOVs of a slide from a sample obtained from a person suffering from a viral infection. The difference in the aggregation of the cells is clearly seen wherein massive aggregation is seen in the sample taken from an individual suffering from bacterial infection as compared to very little or no aggregation in the sample taken from the individual suffering from a viral infection. In addition, the sample taken from the bacterial infection is much more intensely stained than the sample taken from the viral infection due, most probably, due to the fact that the patient with the viral infection has no acute phase response.

FIG. 13 represent a sample prepared in accordance with the invention from a woman suffering from bacterial infection. The leukocytes, erythrocytes and platelet aggregation seen in the picture show a typical picture of a significant inflammatory response.

FIG. 14 represent a sample prepared in accordance with the invention from an individual suffering from a viral infection. The picture reveals aggregation of lymphomononuclear leukocytes but shows no signs of aggregation or intense staining due to an acute phase response which is absent in the viral infection.

Example 5

Results-computerized Analysis

The information acquired from the imaging device may also be transferred prior to, or following an initial analysis by a physician, to a computerized system capable of processing various qualitative and quantitative parameters of the particulate components of the body fluid sample. Such parameters can be for example, a number of white blood cells or a leukocyte adhesiveness/aggregation test (LAAT). These parameters can be assessed using, for example, the inflammation meter application software of the INFLAMET™ system which detects white blood cells based on their color, shape and size characteristics and sorts them into clusters. The results obtained from this computerized analysis may be used in order to evaluate the probability of the existence of an inflammatory reaction in a body fluid sample. Such an existence can be assessed from the presence of, and interactions between, various cellular and non cellular components.

Described below are examples of computerized analysis of various images using the INFLAMET™ system described hereinabove. These examples, represent profiles of differentially distributed particulate components generated from blood samples of several different patients suffering from inflammation caused by variety of inflammatory stimuli.

A typical image analysis process includes the following steps:

(1) Pixel RGB values are converted to HSL (Hue-Saturation-Luminescence) color space.

(2) The luminescent image is "smoothed" using a lowpass filter and its histogram is searched for a "natural" threshold. The natural threshold is found as a value, a preset neighborhood of which (32 levels) has minimal mass, but excluding the top and bottom 10% percentiles of the histogram. The luminescence image is binarized using this threshold, thus yielding a preliminary erythrocyte image.

(3) A pixel in the image is considered a leukocyte candidate, if its hue value lies in a predetermined interval (corresponding to shades of blue-violet) and its saturation is greater than a predetermined threshold.

(4) The binary image consisting of the leukocyte candidate pixels is filtered by a circularly symmetric Gaussian mask with a size proportional to a normal leukocyte diameter. A search is made in the resulting gray-level image for local maxima in a 5×5 pixel area and values which are larger than a predetermined threshold are considered for further processing.

(5) The binary image consisting of leukocyte centers is labeled into connected components (blobs). All blobs with an area greater than a predetermined threshold (8 pixels) are rejected. Only the centroid of other blobs are retained.

(6) The erythrocyte and leukocyte images are matched and logically summarized using the binary "AND" function, and the result is morphologically opened, thus providing a final erythrocyte image.

(7) A plasma image is created by taking the negative of the erythrocyte image. A disk of a 4 micron radius is removed around each leukocyte center from both the erythrocyte and plasma images. The plasma image is twice morphologically eroded with a circular mask of a 3 pixel radius.

(8) All blobs with an area smaller than a predetermined threshold (100 pixels) are eliminated from the erythrocyte image.

(9) All blobs with an area smaller than a predetermined threshold (400 pixels) are eliminated from the erythrocyte negative image.

(10) Blobs in the erythrocyte negative image are labeled, and the area and boundary curvature for each blob are computed.

(11) The average of the boundary curvature of blobs whose area is larger than half the largest blob area is determined. The reciprocal of this average, which is termed as the mean radius of curvature (RC), is used to quantify the smoothness of plasma blobs.

(12) The sum of perimeter squared of the blobs of the erythrocyte negative image is divided by the sum of their areas. This is divided by $4\pi$ and the result is converted by the function f as follows:

$f(x)=1/(x-1)$ if $x>1$, otherwise $f(x)=10$.

(13) The result is denoted VC, and is used to quantify the roundness of plasma blobs.

(14) The RGB components of pixels in plasma area are histogrammed and the maxima of these histograms are found. The RGB histogram peak triplet is converted to HSL coordinates; the S coordinate is termed protein index and is used to quantify the staining of plasma due to proteins.

(15) The mean gray level of luminance at pixels corresponding to erythrocytes is used to quantify the erythrocyte aggregate homogeneity.

(16) The basic statistics collected for erythrocytes include the following: probability that a pixel is in erythrocyte area (named erythrocyte area percentage), conditional probabilities that a pixel is (is not) in an erythrocyte area given that another pixel is (is not) in an erythrocyte area, calculate as a function of the distance between the two pixels. This enables to calculate the distance, such that the probability P (erythrocyte) adjusts to a preset threshold (0.7). This distance is termed "erythrocyte aggregation radius". Additionally, such a distance could be calculated such that the probability P (not erythrocyte) adjusts to the same threshold. This distance is named "vacuum radius".

(17) Leukocyte centers are merged as follows; any pair of centroids nearer than a preset threshold (3 microns) is replaced by the mean point until there are no more of such pairs to merge, thus, obtaining a final list of leukocyte centers.

(18) Any two centers located nearer than a threshold distance (12.5 microns) are considered to belong to the same cluster. Thus all leukocytes are divided into disjoint clusters.

(19) The basic statistics collected for leukocytes is the histogram of cluster sizes. From this, the total leukocyte number and the percentage of leukocytes in aggregates (or in aggregates larger than a preset count) are calculated.

(20) Leukocyte are classified as "far", "near" or "inside" with respect to the erythrocyte aggregate area. Considering this classification procedure as taken together with the classification into isolated vs. aggregated leukocytes, leukocytes are actually divided into six categories.

The processing algorithm leading to this classification is effected as follows. A circle around the center of a leukocyte of a diameter of 12 $\mu$m is considered. The pixels nearest to this circle are classified as erythrocyte aggregates or not. The leukocyte is considered as "far", if the proportion of the erythrocyte related pixels on the circle falls below a threshold (10%). The leukocyte is considered as "inside", if the proportion of the erythrocyte related pixels on the circle is higher than a threshold (60%), or if the largest angular sector of non-erythrocyte pixels on the circle falls below a threshold (25%). In all other cases, the leukocyte is considered as "near".

The above detailed description represent one possible algorithm for processing a stained blood sample. Data processing for an unstained blood sample is generally similar to that of the stained blood sample.

In an unstained sample, the criteria for leukocyte candidate pixels (step 3 above) must be changed to take into account the lack of staining. To this end, the following scheme can be used.

Accumulate histogram of red minus green for pixels in erythrocyte area and set a threshold such that a predetermined proportion (0.01) of this histogram falls below it.

The criteria for candidate pixels can be represented as follows:

luminance>predetermined (200) AND red—green<Threshold
OR
luminance>predetermined (160) AND red—green<predetermined (15)
OR
luminance>predetermined (120) AND red—green<predetermined (0)

Following determination of leukocyte centers (step 5 above), more tests are conducted in order to confirmed these cells as true leukocytes.

These tests consist of the following:

(a) Dark boundary test: in at least 6 out of 8 directions, when moving outward from a leukocyte center one must encounter a pixel darker [having luminance lower by predetermined constant (20)] than the center point of a predetermined distances between leukocyte centers (1 to 5 microns).

(b) Size test: the average radius at which the dark boundary is found, must be greater than a threshold (2 microns).

Example 6

Clinical Examples

The present invention was utilized in order to assess the presence or the absence and the severity of an inflammatory response in a variety of patients.

Profiles obtained according to the teachings of the present invention from various patients were assessed for indications of an inflammatory response and compared to data acquired via prior art diagnostic techniques.

A 72 year old woman was hospitalized with a five day fever, chills and urinary symptoms. She presented leukocytosis of 17000 cells/mm$^3$ (normal≦10500 cells/mm$^3$) and a shift to the left in the differential count. The erythrocyte sedimentation rate was 99 mm per hour and the markers of the acute phase response including CRP, fibrinogen, haptoglobin, gamma globulins as well as ferritin were increased. Three out of three blood cultures taken from the patient as well as the urinary culture were positive for *E. coli*. A typical blood sample profile showing a significant inflammatory response including leukocyte, erythrocyte and platelet aggregation is illustrated by FIG. 13.

A 32 year old man was hospitalized with a one week fever, sore throat, lymphadenopathy and splenomegaly. The blood test revealed 17000 leukocytes/mm$^3$ and lymphomonocytosis. The patient erythrocyte sedimentation was normal and there was no evidence of an acute phase response. The patient recovered with no specific treatment and had positive serology for infectious mononucleosis. The profile illustrated in FIG. 14 reveals aggregation of lymphomononuclear leukocytes and no acute phase response.

A study comparing the diagnostic capabilities of the system of the present invention to routine white blood cell count (WBCC) was also undertaken.

The study included 121 patients with an acute non-viral infection/inflammation including patients having a urinary tract infection, pneumonia, gastroenteritis, meningitis and more. The mean±S.D. patient age was 64±21 years.

The control group included 81 healthy members of the medical staff 31 ±9 years of age as well as 50 patients 63±13 years of age hospitalized due to chest pain and having no history of a recent infection/inflammation or evidence of an acute myocardial infarction.

The total WBCCs and differentials were evaluated by the Coulter S+ analyzer. It was shown that 40 out of the 121 patients had a WBCC level within the normal range and 81 of the patients had a WBCC level above that of the healthy individuals.

Table 1 hereinbelow represents data obtained using the system of the present invention. As is clearly shown therein, the present invention enables to detect an inflammatory response even in cases where prior art techniques fail to provide such a detection.

A cut off point of 18% (M+1 S.D.) aggregation was calculated according to data obtained from healthy individuals. Of the 40 patients having an acute non-viral infection/inflammation and no leukocytosis, a group which included 62% of the patients had values of aggregation higher than the threshold value, while a group representing 38% of the patients had an aggregation value higher than 24% which is ≧2 S.D. above that of healthy individuals.

The above results clearly demonstrate that analyzing white blood cell aggregation according to the teachings of the present invention can be utilized for detecting non-viral infection/inflammation even in individuals which do not have leukocytosis. FIGS. 15a–c are images obtained from samples of individuals suffering from mild, moderate and severe inflammation according to the teachings of the present invention.

TABLE 1

|  | Control | p value | Non-viral infection/inflammation WBCC < 10500 per cm$^2$ | p value | Non-viral infection/inflammation WBCC > 10500 per cm$^2$ |
|---|---|---|---|---|---|
| WBCC (cells per cm$^2$) | 7270 ± 1598 n = 126 (3900–10900) | <0.0001 | 8406 ± 1668 n = 40 (4000–10400) | <0.0001 | 15808 ± 5178 n = 81 (10700–38900) |
| Aggregation % | 11.8 ± 6 n = 56 (60–263) | <0.0001 | 22 ± 8.4 n = 40 (4–44) | <0.0001 | 30 ± 11 n = 81 (5–65) |

WBCC was determined using Coulter S + auto analyzer
% Aggravation was measured in accordance with the present invention.

A comparison study was performed using peripheral blood samples obtained from 75 children with acute febrile conditions as well as from 16 non-febrile children (controls). The children were examined at the Shaare Zedek Medical Center in Jerusalem and blood samples obtained therefrom were screened by system of the present invention for white blood cell aggregates. Results were compared to WBCC values obtained by electronic counter. The children were divided into the following four groups:

(i) Acute bacterial infection: children having lobar pneumonia, acute pyelonephritis or other acute bacterial infections with positive cultures.

(ii) Acute viral infections: children who were evaluated because of an acute febrile disease suggestive of viral etiology, with additional evidence being provided by serology or negative cultures. All the children in this group recovered without receiving any antibiotic treatment.

(iii) Acute febrile disease: children in which clinical diagnosis was uncertain.

(iv) Controls: nonfebrile children who were evaluated before undergoing elective surgery (e.g. herniorrhaphy).

Sampling and analysis of WBCC and differential counts were performed by using EDTA containing tube and the Coulter STKS electronic cell counter. Standard reference values for age-adjusted normal values of the leukocyte counts were used. Slides were prepared from samples obtained from the children in accordance with the teachings of the present invention and the quantification of white blood cells and white blood cell aggregation was carried out as described above.

The results of this study showed that the system of the present invention enables accurate identification of an acute bacterial infection even in cases where a WBCC falls within accepted normal limits.

For example, a child which tested as having a very low WBCC presented the highest leukocyte count and white blood cell aggregation of all tested subjects when his peripheral blood was analyzed in accordance with the present invention (FIG. 16).

Due to the low WBCC electronic count, the child received no antibiotic treatment during the first 24 hours of his stay at the Department of Pediatrics since the clinicians assumed that he suffered from a viral infection. One day following his admission, a scarlatiniform rash appeared all over his body, he had a strawberry tongue and the throat culture revealed extensive growth of group A. streptococci. Following intravenous administration of penicillin, there was a rapid improvement in the child's condition.

The above results clearly indicate that the determination of the number of leukocytes and the level of aggregation in a blood sample effected by the system of the present invention may assist in correct and quick diagnosis of a patient's condition.

An additional comparison study was performed on a different group of subjects. A total of 496 patients with various conditions of infection/inflammation (289 men and 207 women with a mean age of 62±24 years) and 112 controls (70 men and 43 women with a mean age of 35±14 years) participated in the study. Samples from the patients of healthy individuals were obtained and slides were prepared as described hereinabove. The WBCC was carried out using an electronic counter and the number of white blood cells as well as the level of aggregation of white cells in the samples was determined using the method and system of the invention.

The results of the study showed that while an aggregation value of 20% is high for samples taken from healthy individuals, much higher aggregation values were detected in samples obtained from patients suffering from infection/inflammation.

In order to determine the effect of high levels of aggregation on the accuracy of WBCCs obtained by prior art electronic counters, the ratio of the WBCC counted by electron counter (ec WBCC) to the WBCC determined by the present invention (im WBCC) was calculated.

The results demonstrated that in cases of high aggregation, there was a 50% to 60% bias in ec WBCC. In samples in which there was a low level of aggregation (under 10%), it was found that there was a 25% bias in ec WBCC. Thus, at high aggregation levels, the true effect of the aggregation is a 25% bias in the WBCC.

These results show that 10–20% error occurs in electronic WBCC obtained from patients having an increased aggregation of white blood cells.

An additional study was conducted in order to asses the clinical condition of 15 patients suffering from acute infection/inflammation.

Of the 15 patients, 4 had pneumonia, 3 had urinary tract infection, 3 had rheumatoid arthritis, 2 had sepsis, 2 had soft tissue infection and one had Sjogren syndrome. Additional 15 healthy individuals were included as controls.

Table 2 hereinbelow indicates a list of parameters tested by the system of the present invention. As can be seen therein, a significant difference was noted between patients and controls regarding all "conventional variables" as well as those obtained by the present invention. In addition, image analysis revealed a significant correlation between the WBCC and the number of leukocytes per square mm (r=0.67 p<0.0001 n=30), between the LAAT and the concentrations of CRP (r=0.42 p=0.02 n=29) as well as between the EAAT and fibrinogen concentration (r=0.73 p<0.0001 n=27) or ESR (r=0.83 p<0.0001 n=30).

TABLE 2

| "Conventional" variables | Patients | Controls | P = |
|---|---|---|---|
| WBCC (cells/mm$^3$) | 16610 + 7710 | 7810 + 3550 | = 0.001 |
| ESR (mm/h) | 46 + 33 | 8 + 5 | = 0.001 |
| Fibrinogen (mg/dl) | 469 + 146 | 237 + 53 | <0.0001 |
| CRP (mg/L) | 9.9 + 10 | 0.1 + 0.1 | = 0.004 |
| Hgb (g/dl) | 12.9 + 2.4 | 13.9 + 1.2 | NS |
| Variables obtained by image analysis | | | |
| L/mm2 | 173 + 102 | 59 + 23 | = 0.001 |
| LAAT (%) | 18.7 + 12 | 5.3 + 5.3 | = 0.001 |
| EAAT | 23 + 13 | 6 + 3 | <0.0001 |

WBCC = white blood cell count; ESR = erythrocyte sedimentation rate; CRP = C-reactive protein; L/mm2 = leukocytes per square mm by image analysis; LAAT = leukocyte adhesiveness/aggregation test; EAAT = erythrocyte adhesiveness/aggregation test.
N.S. = not significant.

Example 7

Carrier Adhesion

Another important point that has to be taken into consideration when analyzing a blood sample, is the level of cellular adhesion to the carrier. It is known that leukocytes exhibit increased carrier adhesiveness in blood samples which are characterized by increased cellular interactions typical of an inflammatory response (Fier et al., 1999).

Adhesion of cells to a carrier is governed by the presence or absence of specific cell surface molecules which are capable of interacting with molecules adhered to the carrier surface. Thus, by coating the carrier with antibodies or with molecules capable of interacting with the cell surface molecules one can generate an affinity slide which can be used to determine the presence or absence of specific cell types in a biological sample.

For example, if a certain cell type of interest exhibits increased adhesive properties toward a certain type of protein, than a slide coated with such a protein can be used to determine the presence or absence of such a cell in a biological sample. In addition, by using a control slide which is coated with a different and non interacting protein and comparing the two slides, one can produce a differential count which provides an indication as to the level of interaction between the particular protein and particular cell of interest.

FIGS. 17a–b, illustrate parallel analysis of two slides, one coated with antibodies incapable of interacting with an epitope present on the surface of activated platelets (FIG. 17a) and the other with antibodies specific against such an epitope (FIG. 17b).

By simply counting the number of platelets present on each slide, one can determine the level of platelet activation in a blood sample.

It will be appreciated that carriers can be coated with more than one type of protein or interacting molecule to thereby generate multi-track carriers which can be used to correlate the presence of several cell type and to thereby provide a more accurate assessment of a particular condition.

Table 3 which follows lists proteins which can be used to coat carriers, the specificity of each protein, and the information pertaining to a patients condition which can be derived by using a carrier coated with such a protein.

TABLE 3

| Protein | Cell type captured | Disorder |
| --- | --- | --- |
| Collagen | platelets | Thrombosis |
| vWF | platelets | Thrombosis |
| Matrigel | erythrocytes | Thrombosis and inflammation |
| Anti 2B/3A | platelets | Thrombosis |
| Anti CD11b/CD18 | leukocytes | Inflammation |
| Annexin5 | erythrocytes | Thrombosis and inflammation |

Example 8

Volumetric Analysis

The profile described hereinabove is represented by two dimensional (X and Y axis) carrier (substrate) distribution of particulate components such as erythrocyte, leukocyte and/or platelet. Such a profile can also be represented by the distribution of such components in a third dimension (Z-axis), which defines a thickness of the biological sample at various regions on the carrier (also referred to herein as a volumetric profile).

As shown in FIG. 18, a blood sample which is placed on an angled slide and allowed to migrate downwards (towards point 10) under the force of gravity for a predetermined time period, will vary in thickness along the length of the slide (as indicated by points 1–10, FIG. 18).

Variance in thickness and cellular composition at any point along the slide can be correlated with a pathological condition or a disorder. For example, a distributed blood sample of a low hematocrit (indicative of anemia) will be thinner along points 1–10 (FIG. 18) than a distributed blood sample of a high hematocrit (indicative of polycythemia). Such observations can also be represented graphically as is shown in FIG. 19.

Thus, simple and fast analysis of sample thickness at any point on a slide provides information as to the presence or absence of a disorder.

In addition, analysis of the particulate components in regions of varying thickness can also provide valuable information.

Blood sample drawn from a patient suffering from an acute phase response will include sticky proteins such as fibrinogen and gamma globulins. In addition, the patient may develop anemia. Analyzing the thickness of a distributed blood sample will enable detection of such a condition in the presence or absence of anemia.

For example, an anemic blood sample which does not include inflammatory components, will distribute as a thin slice with no significant aggregation of cellular components. In contrast, a blood sample which is anemic and which contains inflammatory components attributed to an acute phase response will exhibit significant cellular aggregation.

By comparing such generated volumetric profiles to profiles of healthy individuals or of the individual a severity of the condition can be assessed.

Such three dimensional or volumetric analysis of distributed biological samples, provides information pertaining to the inter-cellular forces which exist between the cellular components.

For example, as shown in FIGS. 20a–b, when no substantial intercellular cohesive forces exist, a blood sample will distribute evenly along the slide with thickness gradually increasing from top to bottom (FIG. 20a). When significant cohesive forces exist between cells, aggregates form and distribute along the slide. The distribution of aggregates is proportional to their size and composition, with the large or massive aggregates exhibiting the longest migration distances.

By measuring the distribution of the aggregates and the composition and thickness thereof as well as the size of the aggregate free spaces one can assess the health state of an individual from which the blood sample was drawn.

In addition, three dimensional image analysis will enable measuring of the estimated volume of the aggregates and thus will provide data relating to aggregate volume as well as aggregate position on the slide.

Thus, three dimensional analysis provides additional data as compared to the two dimensional analysis described hereinabove.

For example, FIG. 21a–c represent images of the upper (FIG. 21a), middle (FIG. 21b) and lower (FIG. 21c) portions of a slide which is covered with a distributed blood sample.

As is clearly seen therein and as expected, the lower portion of the slide contains more cellular aggregates than the middle or upper portions.

It is interesting to note that although aggregate composition changes along the slide length, the spaces formed in-between the aggregates do not increase in size along the slide length.

Volumetric analysis of slide disposed aggregated cells provides an additional diagnostic value.

As shown in FIGS. 22a–b, when weak intercellular forces exist within a blood sample, the blood stream flowing down the slide (arrow) will not permit the formation of upright cell columns (FIG. 22a). However, in the presence of strong intercellular forces, the blood stream does not flow fast enough to topple cellular columns which are formed (FIG. 22b). Thus, the presence or absence of such columns in a distributed blood sample, can be indicative as to the presence/absence or level of cellular interactions.

The level of interaction is proportional to the intensity of the inflammatory response since it is known that during an inflammatory response cells are activated and as such become sticky. In addition, an increase in sticky plasma proteins further increases the degree of cellular stickiness.

Example 9

Telemedicine Application

The present invention can further be utilized over a communication network in situations were on-site processing of image data can not be effected. For example, data and images produced by the method of the present invention described above can be transmitted via standard telephone lines, or a communication network such as the Internet, to a remote location for image analysis by either a trained physician or technician or by the image analysis software described above.

In such cases, images of the FOVs (fields Of View) can be transferred from a point of image acquisition (e.g. a laboratory) to a remote processing location via a direct upload or e-mail messaging. Following transfer, the images can be viewed and analyzed by a physician and/or automatically analyzed by the software described above and the results can then transferred back to the point of image acquisition as, for example, a table or text file format. In order to avoid transmission errors, a study following all steps of analysis and data transferring was done. Transferred files were transmitted back to the point of acquisition in order to compare them to the original files, and to verify no errors as a result of the transfer were introduced.

More over, the information and data obtained from the imaging device may also be transferred directly or following initial analysis by a physician to a computerized system capable of processing the qualitative and quantitative parameters of the particulate components of the body fluid. This information obtained is further compared to previously stored information of other samples taken at an earlier time from the same individual or to samples taken from healthy or diseased individuals, thus serving as comparative basis for the data which were current collected. The information of the tested sample may also be stored for further use as a base line for comparing additional information in future analysis.

A feasibility study was performed in order to illustrate that images obtained by the system of the present invention can be transmitted via telephone lines to a remote location for analysis.

A total of 30 slides each of 9 FOVs (fields of view) were selected representing a total of 270 images.

Each image was 768 by 576 pixels in size and as such occupied a 1.3 Mbyte file. Following compression (JPEG) each image was represented by a 50 to 70 Kbytes file. An Excel file representing numerical data results obtained from the slide images was 150 Kbytes.

Files were transferred by PC anywhere™ software using an ordinary phone connection using 33.6 kbit/s modems. Transfer errors were not encountered as bit to bit comparison between sent and received images showed no changes.

The transfer of 270 compressed files took a total of 72 minutes, an average of 16 seconds per image file. The transfer of the numerical data (excel file) took 11 seconds, an average of 40 msec per field of view or 0.36 seconds per slide.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents or patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

References

1. Ernst E., Hammerschmidt D. E., Bagge U., Matrai A., Dormandy J. A. Leukocytes and the risk of ischemic diseases. *JAMA* 1987;257: 2318–2324.
2. Froom P., Margaliot S., Caine Y., Benbassat J. Significance of erythrocyte sedimentation rate in young adults. *Am J Clin Pat* 1984;82: 198–200.
3. Cook N. A., Ubben D. Fibrinogen as a major risk factor in cardiovascular disease. *TiPS* 1990;11: 444–448.
4. Ridker P. M., Hennekens C. H., Buring J. E., Rifai N. C-reactive protein and other markers of inflammation in the prediction of cardiovascular disease in women. *N Engl J Med* 2000;342: 836–843.
5. Rotstein R., Zeltser D., Fusman R., Shapira I., Urbach J., Bornstein N. M., Roth A., Keren G., Avitzour D., Arber N., Berliner S. The inflammation meter (INFLAMET): A new diagnostic approach to reveal the presence of an inflammatory response and for the assessment of its intensity. *Isr Med Assoc J* 2000;2: 476–477.
6. Berliner S., Shapira I., Rogowski O., Sadees N., Rotstein R., Fusman R., Avitzour D., Cohen S., Arber N., Zeltser D. Combined leukocyte and erythrocyte aggregation in the peripheral venous blood during sepsis. A clue to the presence of a commonly shared adhesive protein(s). *Int J Clin Lab Res* 2000;30: 27–31.
7. Fusman R., Zeltser D., Rotstein R., Chapman Y., Avitzour D., Shapira I., Eldor A., Elkayam O., Caspi D., Arber N., Berliner S. INFLAMET: an image analyzer to display erythrocyte adhesiveness/aggregation. *Eur J Int Med* 2000;
8. Maharshak N., Kassirer M., Zeltser D., Rotstein R., Rogowski O., Shapira I., Deutch V., Arber N., Eldor A., Berliner S. The inflammation meter: novel technique to detect the presence of infection/inflammation in patients without leukocytosis but with an increased leukocyte adhesiveness/aggregation. *Acta Haematol* 2000;
9. Ensrud K., Grimm H. R. The white blood cell count and risk for coronary heart disease. *Am Heart J* 1992;124: 207–212.
10. Prentice R. L., Szatrowski T. P., Kato H., Mason M. W. Leukocyte counts and cerebrovascular disease. *J Chronic Dis* 1982;35: 703–714.
11. Berliner S., Fishelson Z., Bruhis S., Kaufman H., Pinhas J., Aronson M. The phenomenon of leukergy: induction and detection of leukocyte aggregation in whole human blood. *J Lab Clin Med* 1987;109: 575–582.
12. Zeltser D., Fusman R., Rotstein R., Shapira I., Elkayam O., Chapman Y., Eldor A., Arber N., Berliner S. Gamma globulin induces leukocyte adhesiveness/aggregation and leukopenia; a clue to the presence of pseudoleukopenia. *Am J Med Sci* 2000;
13. Sox H. C., Liang M. H. Erythrocyte sedimentation rate. *Arch Intern Med* 1986;104: 515–523.
14. Danesh J., Collins R., Peto R., Lowe G. D. Haematocrit, viscosity, erythrocyte sedimentation rate: meta-analyses of prospective studies of coronary heart disease. *Eur Heart J* 2000;21: 515–520.
15. Liuzzo G., Biasucci L. M., Gallimore J. R., Grillo R. L., Rebuzzi A. G., Pepys M. B., Maseri A. The prognostic value of C-reactive protein and serum amyloid A protein in severe unstable angina. *N Engl J Med* 1994;331: 417–424.
16. Lentnek A. L., Schreiber A. D., MacGregor R. R. The induction of augmented granulocyte adherence by inflammation. *J Clin Invest* 1976;57: 1098–1103.
17. Arber N., Berliner S., Hallak A., Bujanover Y., Dotan I., Liberman E., Santo M., Moshkowitz M., Ratan J., Dotan G., et a. Increased leukocyte adhesiveness/aggregation is a most useful indicator of disease activity in patients with inflammatory bowel disease. *Gut* 1995;37: 77–80.
18. Berliner S., Fried M., Caspi D., Weinberger A., Yaron M., Pinkhas J., Aronson M. Evaluation of disease activity in rheumatic patients by leucocyte adhesiveness/ aggregation. *Ann Rheum Dis* 1988;47: 458–462.

19. Hadengue A., Razavian S. M., Del-Pino M., Simon A., Levenson J.
    Influence of sialic acid on erythrocyte aggregation in hypercholesterolemia. *Thromb Haemost* 1996;76: 944–949.
20. Lechi C., Zotti M., Carradini P., Bonadonna C., Arozio E., Pedoalli C., Lechi A. Increased leukocyte aggregation in patients with hypercholesterolemia. *Clin Chim Acta* 1984;144: 11–16.
21. Caimi G., Canino B., Romano A., Catania A., Presti L. Erythrocyte aggregation and erythrocyte membrane properties in type 2 diabetes mellitus and in vascular atherosclerotic disease. *Thromb Haemost* 2000;83: 516–517.
22. Elhadd T. A., Bancroft A., McLaren M., Newton R. W., Belch J. J. Increased granulocyte aggregation in vitro in diabetes mellitus. *QJM* 1997;90: 461–464.
23. Fadilah R., Berliner S., Kidron D., Ben B. M., Frumkin R., Jaffe A., Pinkhas J., Aronson M. The state of leukocyte adhesiveness/aggregation in the peripheral blood of patients with respiratory tract infections. *Respiration* 1990;57: 109–113.
24. Razavian S. M., Del-Pino M., Simon A., Levenson J. Increase in erythrocyte disaggregation shear stress in hypertension. *Hypertension* 1992;20: 247–252.
25. Suckfull M., Thiery J., Schom K., Kastenbauer E., Seidel D. Clinical utility of LDL-apheresis in the treatment of sudden hearing loss: a prospective randomized study. *Acta Otolaryngol* 1999;119: 763–766.
26. Sherman D. G., Atkinson R. P., Chippendale T., Levin K. A., Ng K., Futrell N., Hsu C. Y., Levy D. E. Intravenous ancrod for treatment of acute ischemic stroke. The STAT study: a randomized controlled trial. *JAMA 2000;283: 2395–2403*.
27. Berrouschot J., Barthel H., Koster J., Hesse S., Rossler A., Knapp W. H., Schneider D. Extracorporeal rheopheresis in the treatment of acute ischemic stroke. A randomized pilot study. *Stroke* 1999;30: 787–792.
28. Pruefer D., Scalia R., Lefer A. M. Simvastatin inhibits leukocyte-endothelial cell interactions and protects against inflammatory processes in normocholesterolemic rats. *Arterioscler Thromb Vasc Biol* 1999;19: 2894–2900.
29. Maple C., McLaren M., Bancroft A., Ho M., Belch J. J. Dietary supplementation with omega 3 and 6 fatty acids reduces induced white blood cell aggregation in healthy volunteers. *ProstaglandinsLeukot Essent Fatty Acids* 1998;58: 365–368.
30. Galante Scan J. Lab. Clin. Invest. 1992;52: 431–433
31. Fier G, Y Sasson, O Rogowsky, Liberman E, Leibowitz E, Halperin, Sarov J, Arber N, Sarafian F, Seltzer D, Berliner S. Stress in the emergency room: a simple leukocyte to glass adhesion test provides a diagnostic tool to differentiate between stress and infection/inflammation related leukocytosis. Stress Med 1999; 15:183–188.

What is claimed is:

1. A method of determining presence or absence of a clinical condition in an individual, the method comprising:
   (a) causing controlled flow of a body fluid sample of the individual on a substrate, said controlled flow of said body fluid sample leading to a differential distribution of the particulate components on said substrate;
   (b) providing a magnified image of differentially distributed particulate components on said substrate, thereby generating a profile of particulate components in said body fluid sample of the individual; and
   (c) comparing said profile of step (b) with a profile of particulate components of a control body fluid sample obtained under said controlled flow to thereby determine presence or absence of the clinical condition in the individual.

2. The method of claim 1, wherein step (c) comprises comparing said profile of step (b) and said profile of particulate components of a control body fluid sample according to at least one parameter selected from the group consisting of estimated hemoglobin concentration, approximated leukocyte count and differential, approximated platelet count, degree of leukocyte aggregation, aggregate composition, degree of leukocyte, erythrocyte and/or platelet adherence towards the surface of said substrate, degree of red cell aggregation, degree of platelet aggregation, degree of leukocyte to erythrocyte interaction, degree of erythrocyte to platelet interaction and degree of leukocyte to platelet interaction.

3. The method of claim 2, wherein the step of analyzing and optionally characterizing the profile representing said particulate components in said body fluid sample is used for determining the efficiency of a treatment regimen.

4. The method of claim 1, wherein the clinical condition is caused by an agent selected from the group consisting of an infective agent and a chemical agent.

5. The method of claim 1, wherein the clinical condition is caused by a disorder selected from the group consisting of atherosclerosis, diabetes viral infection and bacterial infection.

6. The method of claim 1, further comprising the step of converting said magnified image into data prior to step (c).

7. The method of claim 1, wherein said body fluid sample of the individual is a peripheral blood sample.

8. The method of claim 1, wherein said step of causing controlled flow of said body fluid sample on a substrate is effected by a holder capable of holding said substrate in an essentially angled position, or by a centrifuge.

9. The method of claim 1, further comprising staining the particulate components on said substrate prior to step (b).

10. A method of determining presence or absence of an atherosclerosis risk factor in an individual, the method comprising the steps of:
    (a) causing controlled flow of a body fluid sample of the individual on a substrate, said controlled flow of said body fluid sample leading to a differential distribution of particulate components included in said body fluid sample on said substrate;
    (b) providing a magnified image of differentially distributed particulate components on said substrate, thereby generating a profile of particulate components in said body fluid sample of the individual; and
    (c) comparing said profile of step (b) with a profile of particulate components of a control body fluid sample obtained under said controlled flow to thereby determine presence or absence of the atherosclerosis risk factor in the individual.

11. The method of claim 10, wherein step (c) comprises comparing said profile of step (b) and said profile of particulate components of a control body fluid sample according to at least one parameter selected from the group consisting of a number of white blood cells, leukocytes adhesiveness/aggregation state (LAAT) and erythrocytes adhesiveness/aggregation state (EAAT).

12. The method of claim 10, further comprising the step of converting said magnified image into data prior to step (c).

13. The method of claim 10, wherein said body fluid sample of the individual is a peripheral blood sample.

14. The method of claim 10, wherein said step of causing controlled flow of said body fluid sample on said substrate is effected by a holder capable of holding said substrate in an essentially angled position or a centrifuge.

15. The method of claim 10, further comprising staining the particulate components included in said body fluid sample prior to step (b).

16. A method of generating a profile of a body fluid sample of an individual comprising the steps of:
   (a) causing controlled flow of the body fluid sample on a substrate, said controlled flow of the body fluid sample leading to a distribution of the body fluid sample on said substrate; and
   (b) determining a thickness variance of the body fluid sample along a direction of said controlled flow on said substrate, thereby generate the profile of the body fluid sample of the individual; and
   (c) comparing the profile of step (b) with a profile of a control body fluid sample obtained under said controlled flow.

17. The method of claim 16, further comprising the step of analyzing and optionally characterizing particulate components of said body fluid sample in at least one specific region of said substrate.

18. The method of claim 17, wherein said step of analyzing and optionally characterizing particulate components in said body fluid sample is effected according to at least one parameter selected from the group consisting of estimated hemoglobin concentration, approximated leukocyte count and differential, approximated platelet count, degree of leukocyte aggregation, aggregate composition, degree of leukocyte, erythrocyte and/or platelet adherence towards the surface of said substrate, degree of red cell aggregation, degree of platelet aggregation, degree of leukocyte to erythrocyte interaction, degree of erythrocyte to platelet interaction and degree of leukocyte to platelet interaction.

19. The method of claim 16, wherein said profile of the body fluid sample is used for determining a presence or absence of a clinical condition in an individual.

20. The method of claim 17, wherein the step of analyzing and optionally characterizing particulate components of said body fluid sample in said at least one specific region of said substrate is used for diagnosing a disorder in an individual.

21. The method of claim 19, wherein said clinical condition is caused by an agent selected from the group consisting of an infective agent and a chemical agent.

22. The method of claim 19, wherein said clinical condition is caused by a disorder selected from the group consisting of atherosclerosis, diabetes viral infection and bacterial infection.

23. The method of claim 16, wherein said body fluid sample is a peripheral blood sample.

24. The method of claim 16, wherein said step of causing controlled flow of said body fluid sample on a substrate is effected by a holder capable of holding said substrate in an essentially angled position, or by a centrifuge.

25. The method of claim 1, wherein said magnified image is of said differential distribution of said particulate components along at least one axis selected from the group consisting of an axis along a length of said substrate, an axis along a width of said substrate and an axis perpendicular to said substrate.

26. The method of claim 1, wherein said control body fluid sample is derived from an individual which is healthy.

27. The method of claim 1, wherein said control body fluid sample is derived from an individual having the clinical condition.

28. The method of claim 10, wherein said magnified image is of said differential distribution of said particulate components along at least one axis selected from the group consisting of an axis along a length of said substrate, an axis along a width of said substrate and an axis perpendicular to said substrate.

29. The method of claim 10, wherein said control body fluid sample is derived from an individual which is healthy.

30. The method of claim 10, wherein said control body fluid sample is derived from an individual having the atherosclerosis risk factor.

31. The method of claim 10, wherein said control body fluid sample is derived from an individual which is healthy.

32. The method of claim 16, wherein said control body fluid sample is derived from an individual having a clinical condition.

* * * * *